(12) United States Patent
Manzella, Jr. et al.

(10) Patent No.: US 8,955,168 B2
(45) Date of Patent: *Feb. 17, 2015

(54) SURGICAL PROTECTIVE SYSTEM HEAD GEAR ASSEMBLY INCLUDING HIGH VOLUME AIR DELIVERY SYSTEM

(75) Inventors: Salvatore Manzella, Jr., Barrington, IL (US); David K. Platt, Mt. Prospect, IL (US); Michael C. Shaughnessy, Arlington Heights, IL (US); Kevin T. Pullen, Bowie, TX (US); Keith A. Larson, Libertyvile, IL (US); Alison J. Sanders, Rancho Mirage, CA (US)

(73) Assignee: Ecolab USA Inc., St. Paul, MN (US)

( * ) Notice: Subject to any disclaimer, the term of this patent is extended or adjusted under 35 U.S.C. 154(b) by 14 days.

This patent is subject to a terminal disclaimer.

(21) Appl. No.: 13/468,611

(22) Filed: May 10, 2012

(65) Prior Publication Data
US 2012/0216341 A1    Aug. 30, 2012

Related U.S. Application Data

(60) Division of application No. 12/882,707, filed on Sep. 15, 2010, now Pat. No. 8,196,224, which is a continuation of application No. 11/463,074, filed on Aug. 8, 2006, now Pat. No. 7,937,775, which is a continuation-in-part of application No. 11/199,716, filed on Aug. 9, 2005, now abandoned.

(51) Int. Cl.
| | | |
|---|---|---|
| *A42B 1/06* | (2006.01) | |
| *A41D 13/002* | (2006.01) | |
| *A41D 13/11* | (2006.01) | |
| *A41D 13/12* | (2006.01) | |
| *A42B 3/28* | (2006.01) | |
| *A61B 19/00* | (2006.01) | |
| *A62B 18/04* | (2006.01) | |
| *A61B 19/08* | (2006.01) | |
| *A61F 9/02* | (2006.01) | |

(Continued)

(52) U.S. Cl.
CPC ............ *A41D 13/0025* (2013.01); *A41D 13/11* (2013.01); *A41D 13/1209* (2013.01); *A42B 3/286* (2013.01); *A61B 19/26* (2013.01); *A62B 18/045* (2013.01); *A61B 19/08* (2013.01); *A61B 19/42* (2013.01); *A61B 2019/262* (2013.01); *A61B 2019/385* (2013.01); *A61F 9/029* (2013.01); *A62B 17/04* (2013.01); *A62B 18/082* (2013.01)
USPC .......................................................... 2/410

(58) Field of Classification Search
USPC ...................... 2/422, 456, 416, 424, 7, 171.3; 128/201.22, 201.25, 206.12; 607/107
See application file for complete search history.

(56) References Cited

U.S. PATENT DOCUMENTS

| | | | | |
|---|---|---|---|---|
| 1,996,499 A | * | 4/1935 | Young .............................. | 165/99 |
| 3,181,532 A | * | 5/1965 | Harris ....................... | 128/201.23 |
| 3,822,698 A | * | 7/1974 | Guy .......................... | 128/201.25 |

(Continued)

*Primary Examiner* — Richale Quinn
(74) *Attorney, Agent, or Firm* — Amy J. Hoffman

(57) ABSTRACT

A surgical protective assembly having an air movement device and a head gear assembly carrying the air movement device. The head gear assembly includes an outer wall, an inner wall, a front end, a back end and a middle portion between the front end and the back end. The outer wall has an upper opening, the inner wall has an array of openings, and the inner and outer wall define a front opening at the front end. The head gear assembly has a passageway that fluidly connects together, the upper opening, the array and the front opening.

12 Claims, 25 Drawing Sheets

(51) Int. Cl.
*A62B 17/04* (2006.01)
*A62B 18/08* (2006.01)

(56) References Cited

U.S. PATENT DOCUMENTS

| | | | | |
|---|---|---|---|---|
| 4,483,021 A | * | 11/1984 | McCall | 2/7 |
| 4,744,106 A | * | 5/1988 | Wang | 2/7 |
| 4,869,250 A | * | 9/1989 | Bitterly | 607/107 |
| 4,901,716 A | * | 2/1990 | Stackhouse et al. | 128/201.25 |
| 5,042,474 A | * | 8/1991 | Williamson | 128/206.12 |
| 5,054,480 A | * | 10/1991 | Bare et al. | 128/201.25 |
| 5,085,231 A | * | 2/1992 | Johnson | 131/329 |
| 5,113,853 A | * | 5/1992 | Dickey | 128/200.28 |
| 5,592,936 A | * | 1/1997 | Thomas et al. | 128/206.12 |
| 5,711,033 A | * | 1/1998 | Green et al. | 2/171.3 |
| 5,887,281 A | * | 3/1999 | Green et al. | 2/171.3 |
| 6,122,773 A | * | 9/2000 | Katz | 2/171.3 |
| 6,374,823 B1 | * | 4/2002 | Hajianpour | 128/201.22 |
| 6,393,617 B1 | * | 5/2002 | Paris et al. | 2/171.3 |
| 6,481,019 B2 | * | 11/2002 | Diaz et al. | 2/171.3 |
| 6,622,311 B2 | * | 9/2003 | Diaz et al. | 2/171.3 |
| 6,792,944 B1 | * | 9/2004 | Green et al. | 128/201.22 |
| 6,973,677 B2 | * | 12/2005 | Diaz et al. | 2/171.3 |
| 2007/0089221 A1 | * | 4/2007 | Manzella et al. | 2/456 |

* cited by examiner

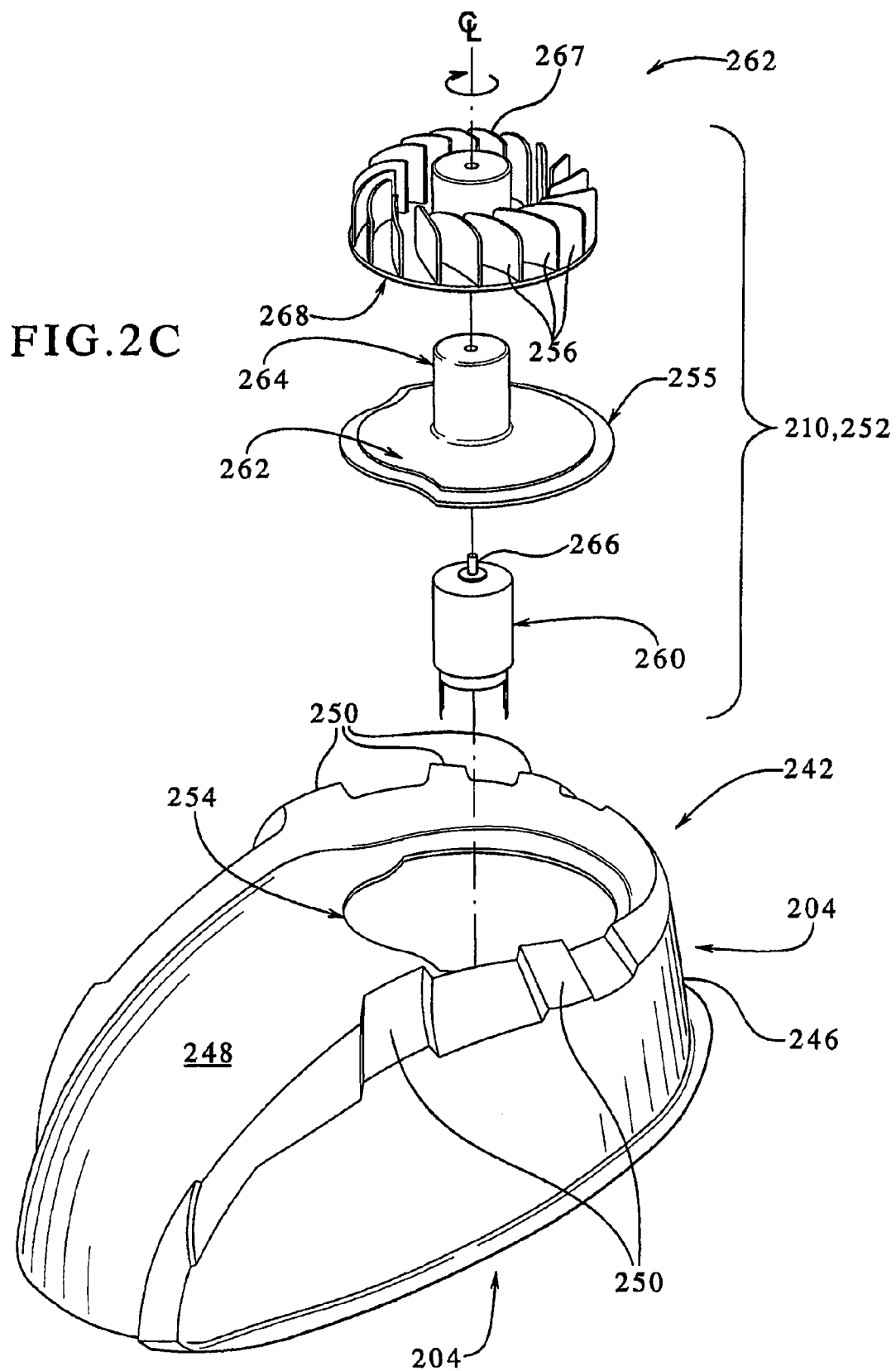

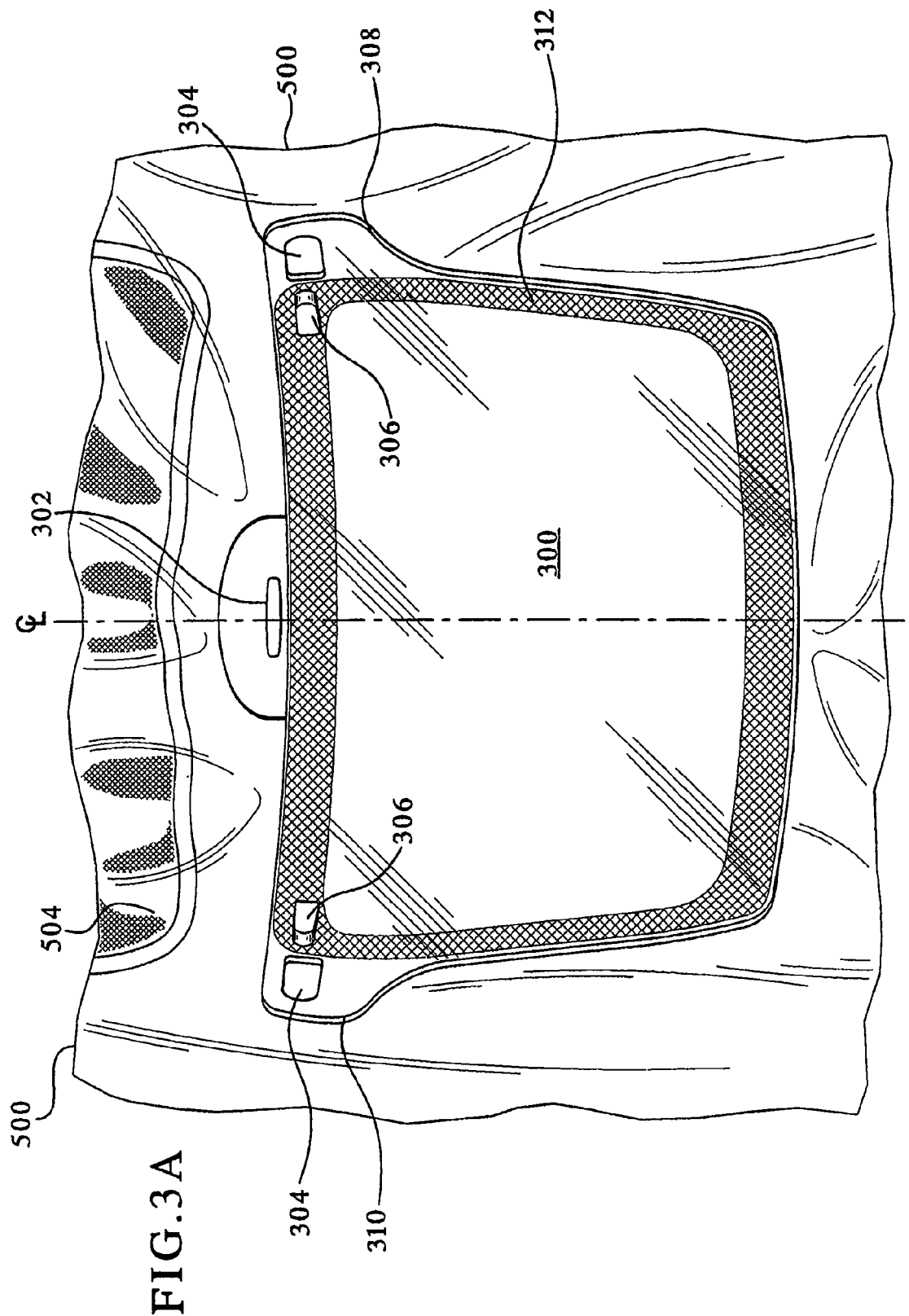

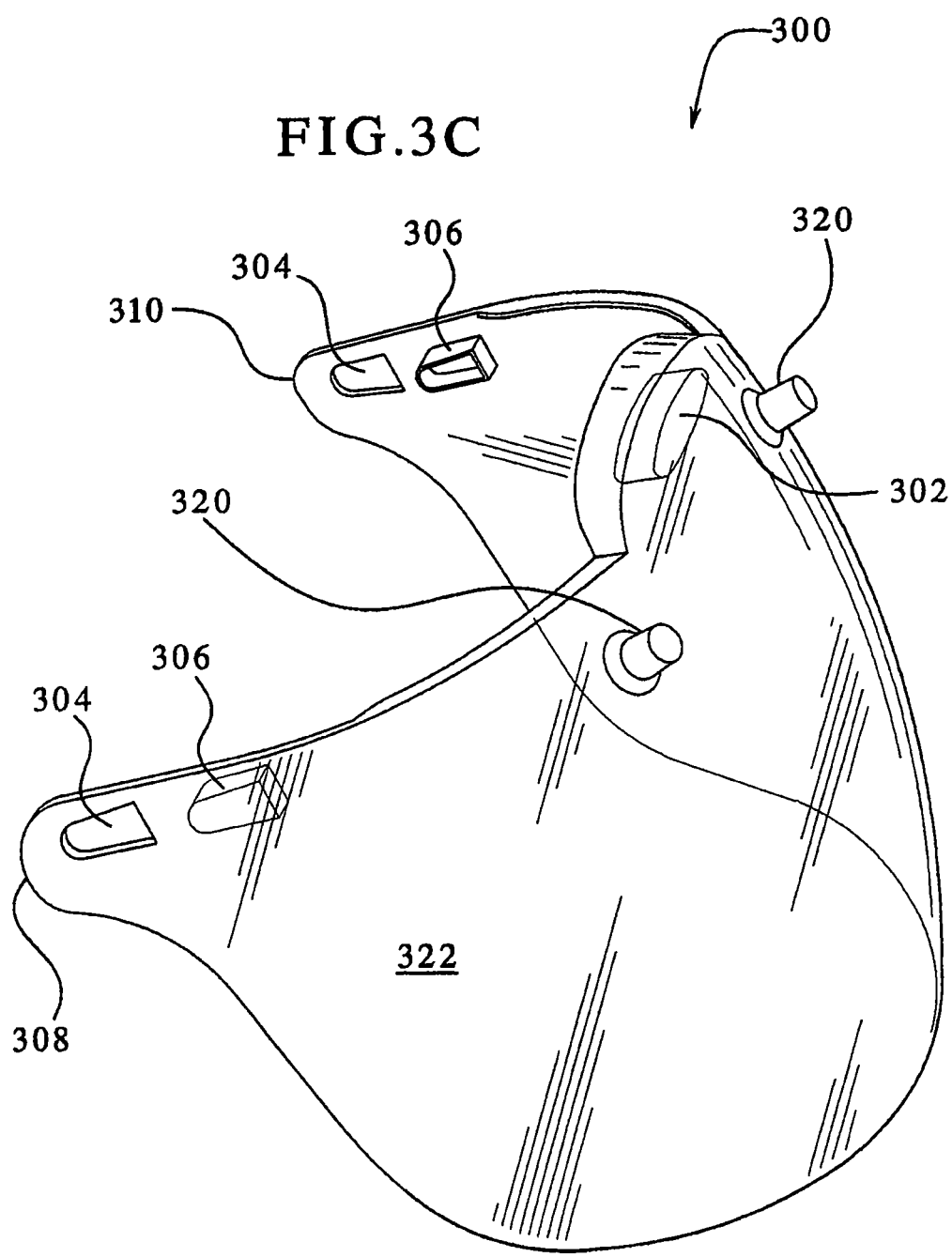

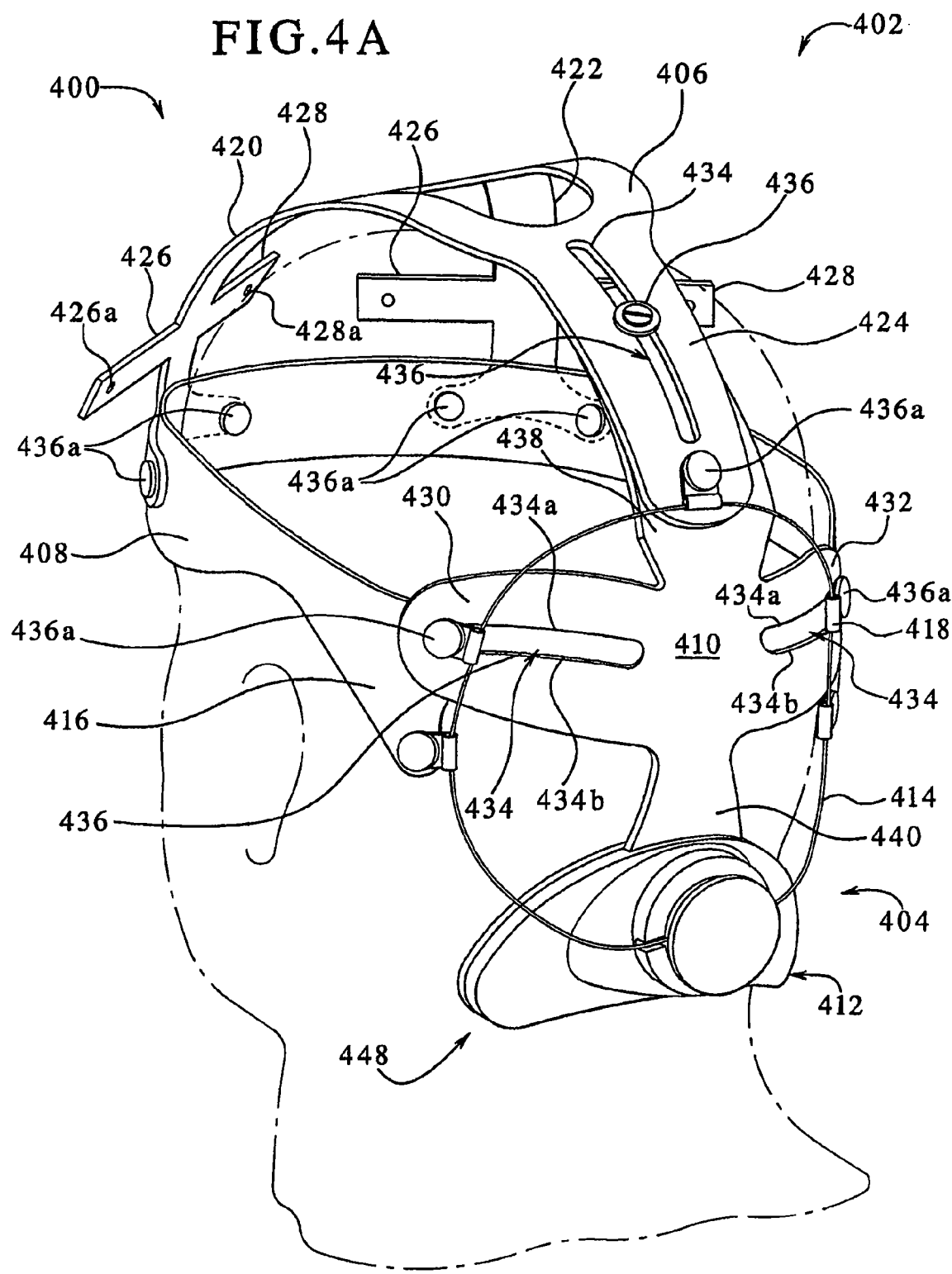

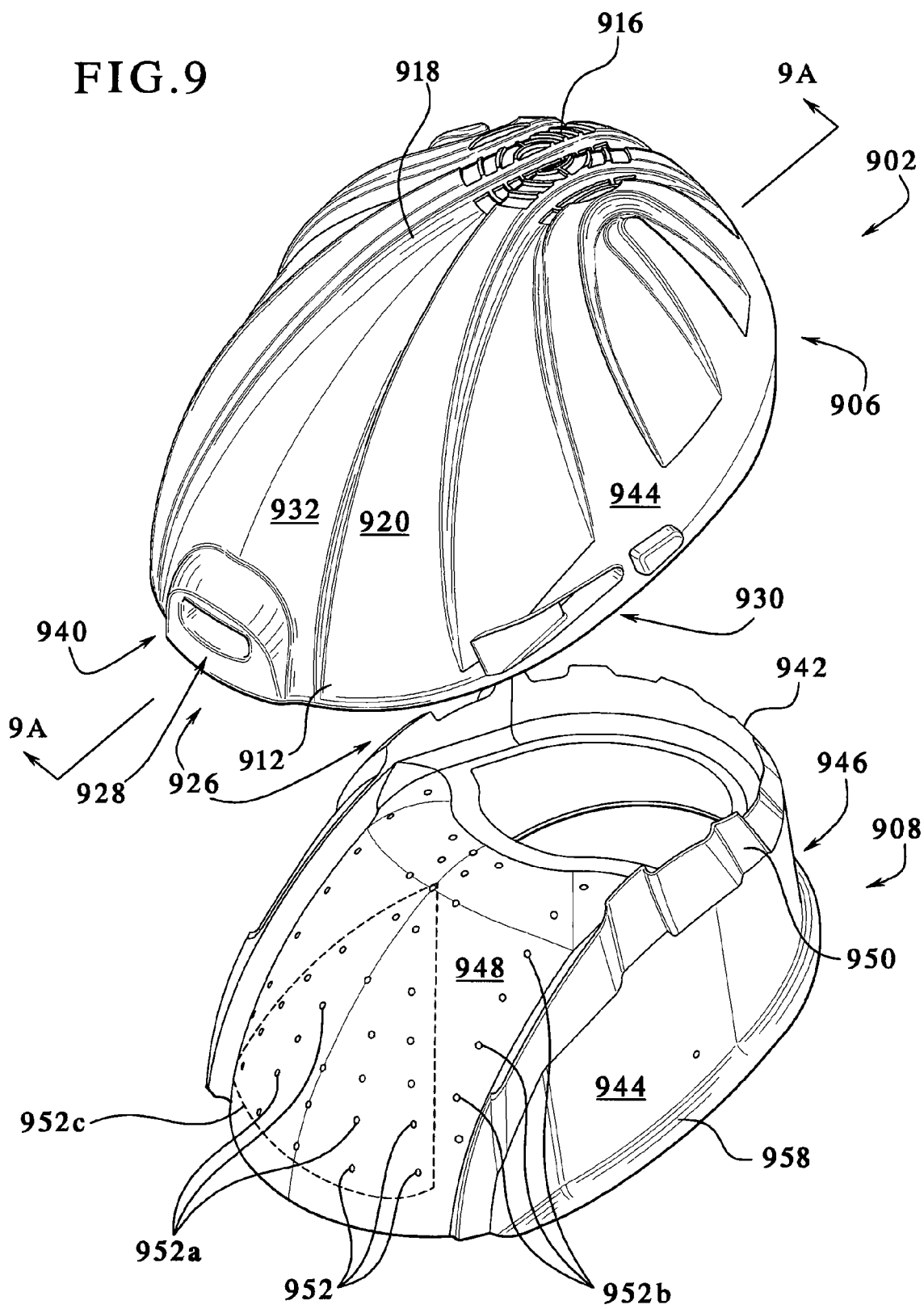

SURGICAL PROTECTIVE SYSTEM HEAD GEAR ASSEMBLY INCLUDING HIGH VOLUME AIR DELIVERY SYSTEM

PRIORITY CLAIM

This patent is a divisional of, and claims the benefit of priority of, U.S. patent application Ser. No. 12/882,707, entitled "Surgical Protective System And Assembly Having A Head Gear Assembly Supporting A Surgical Garment And Air Delivery System," filed on Sep. 15, 2010, now allowed which claims priority to and is a continuation of U.S. patent application Ser. No. 11/463,074 which is a continuation in part of U.S. patent application Ser. No. 11/199,716, filed Aug. 9, 2005, now abandoned, the entire contents of which are hereby incorporated by reference in their entirety for all purposes.

BACKGROUND

When surgeons operate, it is possible that blood, bodily fluids, bacteria, viruses and air borne pathogens and particles can travel from the patient to the surgeon. It is also possible that certain fluids and particles, such as sweat drops and hair, can fall from the surgeon into the surgical site of the patient. In each case, the surgeon and the patient are exposed to the possibility of acquiring an infection or disease. For these reasons, there is a need for advancements in surgical equipment to help protect both the surgeon and patient from these risks while maintaining suitable operating conditions and comfort for the surgeon.

SUMMARY OF THE INVENTION

The surgical protective system and assembly described herein generally relates to a protective system, and more particularly to a surgical personal protective assembly that includes an adjustable helmet or head gear assembly configured to deliver a relatively high volume of air flow to a user or wearer via an air delivery system. The disclosed surgical protective assembly is intended to be worn on a user's head and is well-suited for use in a sterile environment such as an operating room or a clean room where exposure to contaminants can have undesirable consequences.

The adjustable helmet is configured to cooperate with a surgical garment and face shield to protect the user and the patient against airborne debris, pathogens or contaminants and while delivering and circulating filtered air to and around the user's face and the crown or top of the user's head to help maintain personal comfort and a suitable climate for the user.

Additional features and advantages of the present invention are described in, and will be apparent from, the following Detailed Description and the figures.

BRIEF DESCRIPTION OF THE FIGURES

FIG. 2C is an exploded perspective view of one embodiment of an air movement device and a fragmentary portion of the inner shell.

FIG. 3A is an interior plan view of the face shield shown in FIG. 3 illustrating the attachment of one embodiment of a surgical garment.

FIG. 3C is an exterior perspective view of one embodiment of a face shield including attachment points or mounts for affixing accessories thereto.

FIG. 4A is a rear perspective view of one embodiment of the adjustable head securing assembly.

FIG. 9 is an exploded perspective view of another embodiment of the head gear assembly illustrating one embodiment of a shell unit having an outer wall aligned above an inner wall prior to assembly.

DETAILED DESCRIPTION

I. Overview of the Surgical Protective Assembly

Figure 1:
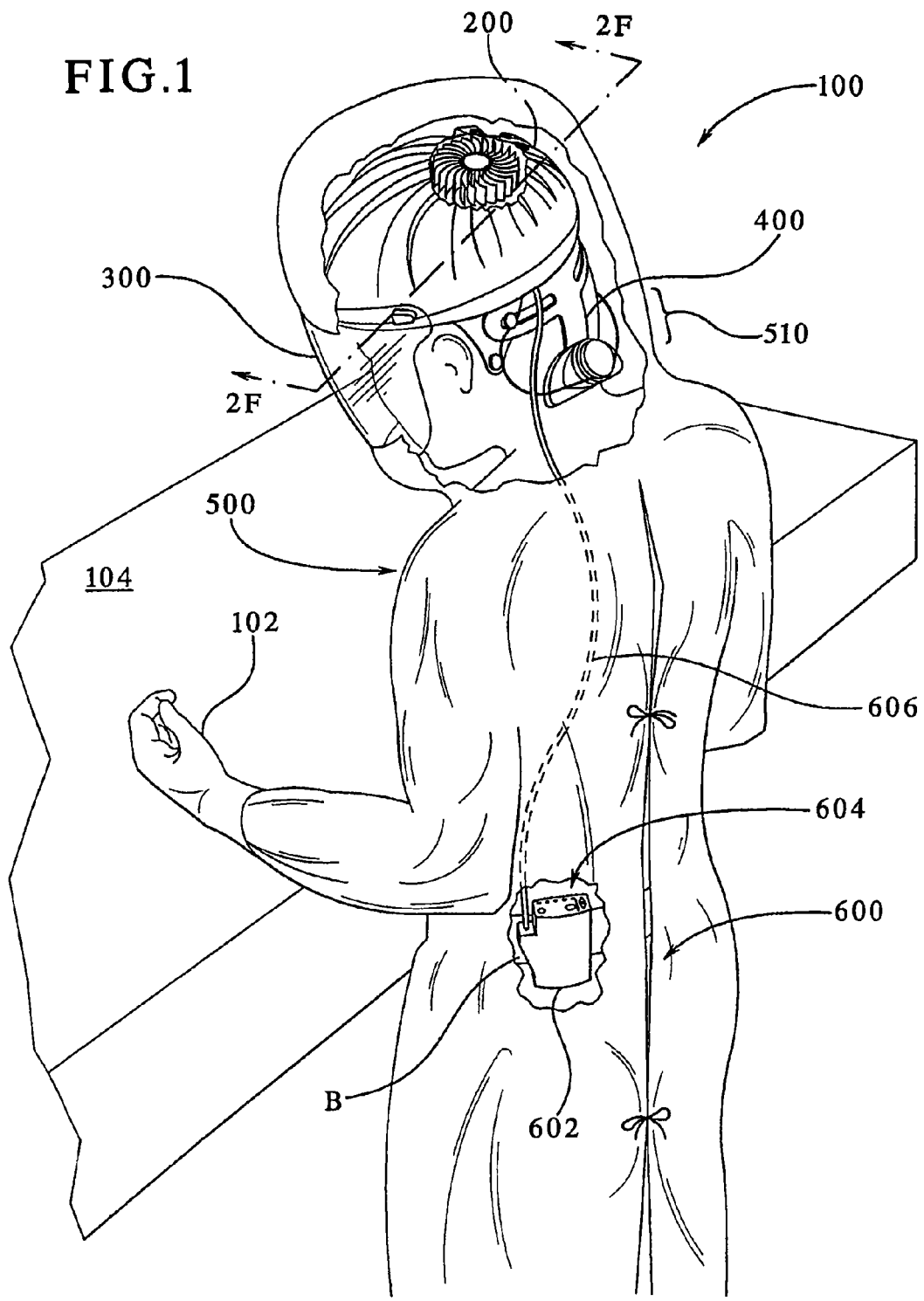
FIG. 1 is a rear perspective view of one embodiment of the surgical protective assembly in use during a medical procedure.

Turning to the figures, FIG. 1 illustrates one embodiment of a surgical protective assembly 100. The surgical protective assembly 100 includes several assemblies, subassemblies and components which can be interconnected and combined to form a single assembly or system. In particular, the surgical protective assembly 100 includes: (a) a head gear assembly 200; (b) a face shield 300 removably attachable to the head gear assembly 200; (c) an adjustable head securing assembly 400 attached to the head gear assembly 200; (e) a surgical garment 500 attachable to the head gear assembly 200 and face shield 300; (f) a control device 600 operatively coupled to the head gear assembly 200; and (g) a battery charger or battery charge device 700 (see FIG. 7) which is operable with the a plurality of control devices which are the same as control device 600.

As illustrated in FIG. 1, a user 102 can wear and use the components of the surgical protective assembly 100 to perform a task on a working surface 104. Specifically, the adjustable head securing assembly 400 fits snuggly on the user's head and supports the head gear assembly 200 and the face shield 300 which cover the top of the user's head and protect the front of the user's face. Moreover, the surgical garment 500 can be used to cover the other components and assemblies of the protective system 100 while being arranged to protect the torso, arms and lower body of the user 102. Thus, as illustrated in this embodiment, the surgical garment 500, the head gear assembly 200 and face shield 300 cooperate to increase the protection of the user 102 from debris and contaminants that may be encountered on the working surface 104 and in the environment. Likewise, the surgical garment 500, the head gear assembly 200 and face shield 300 cooperate to increase the protection of a patient resting on the working surface 102 against debris and contaminants that may fall from the user 102 into the surgical site of the patient.

II. Head Gear Assembly

Figure 2:
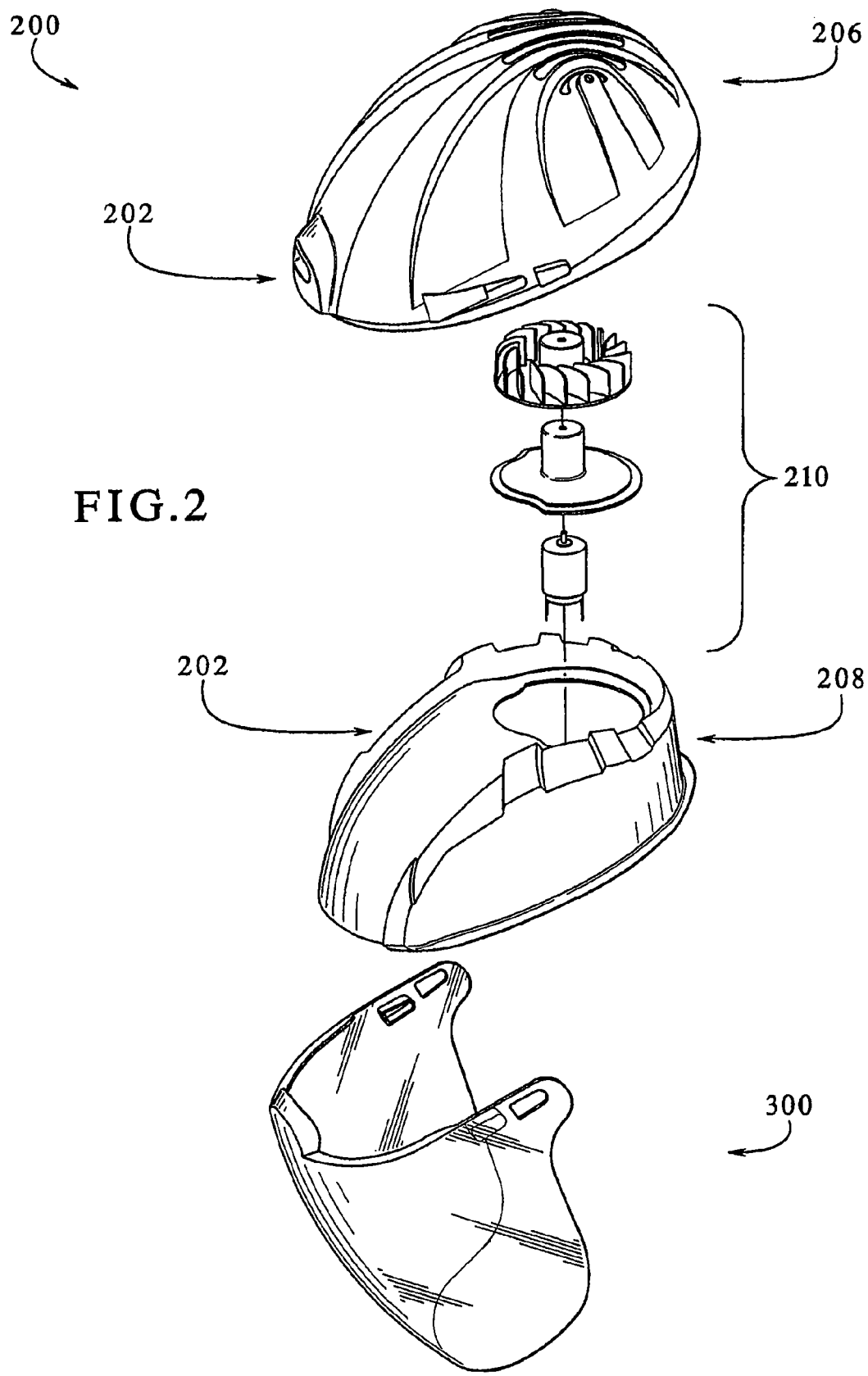
FIG. 2 is an exploded view of one embodiment of the helmet or head gear assembly.
Figure 2A:
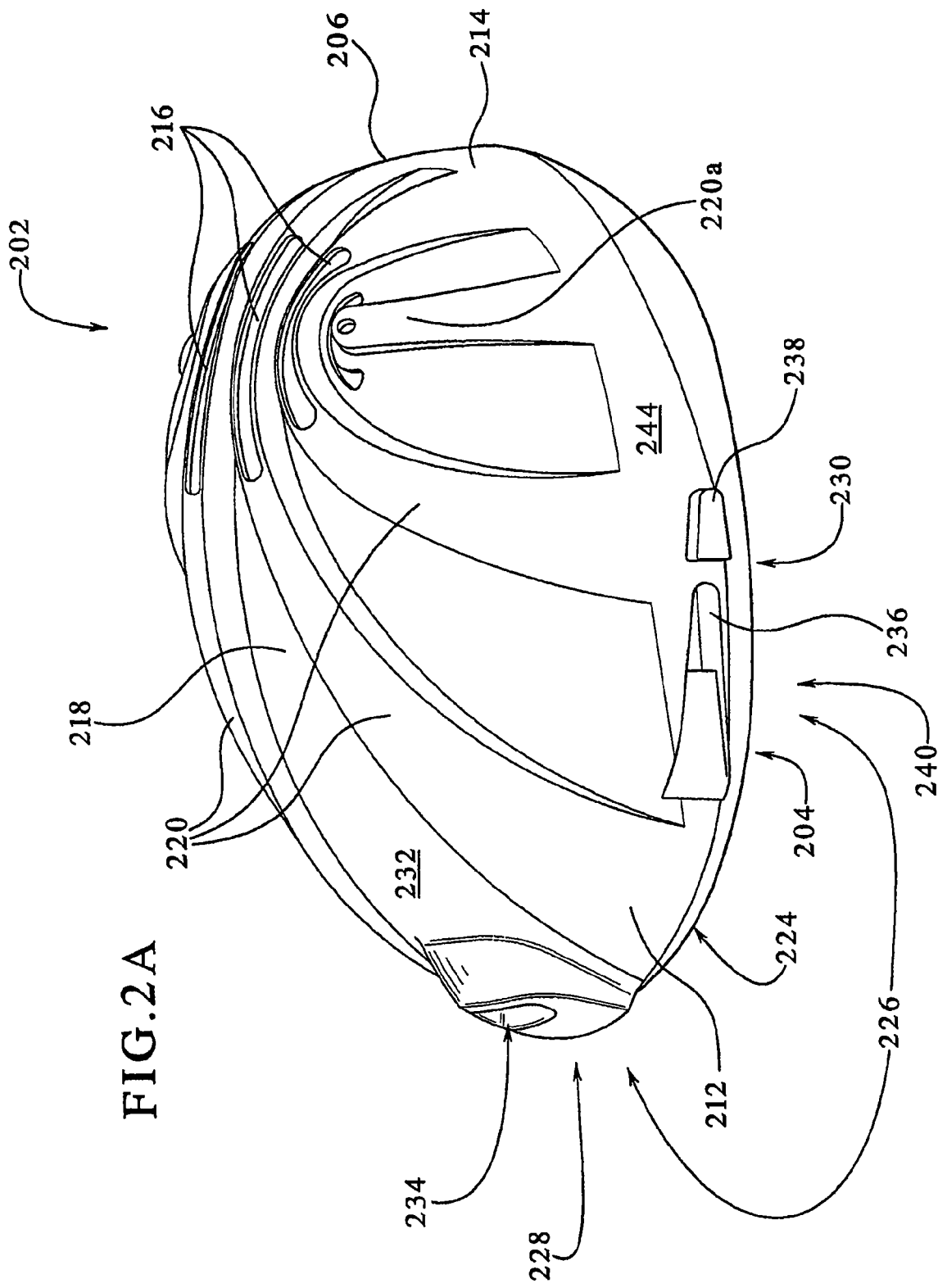
FIG. 2A is an enlarged perspective view of one embodiment of the outer shell of the head gear assembly.
Figure 2B:
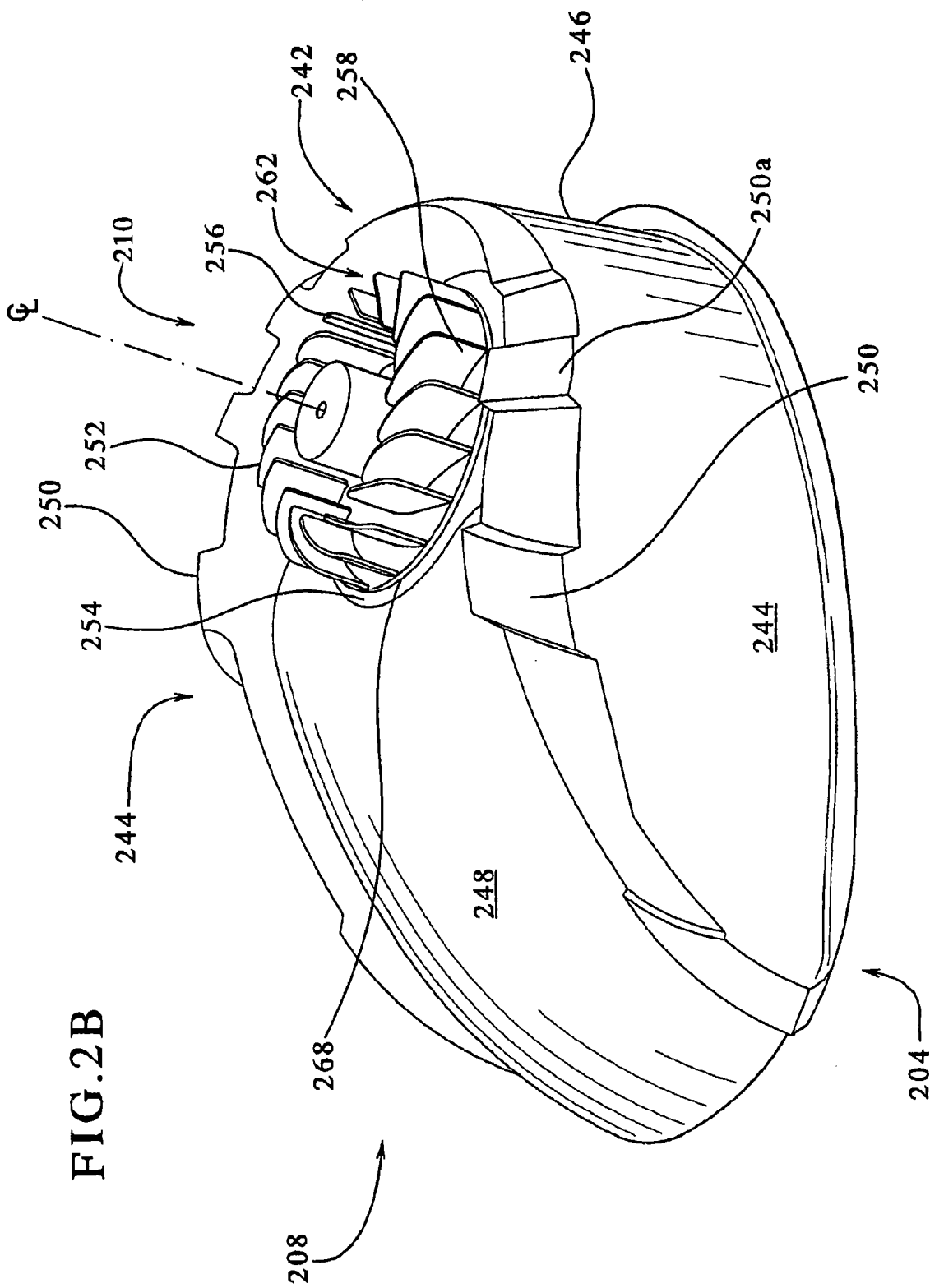
FIG. 2B is an enlarged perspective view of one embodiment of an inner shell of the head gear assembly.
Figure 2D:
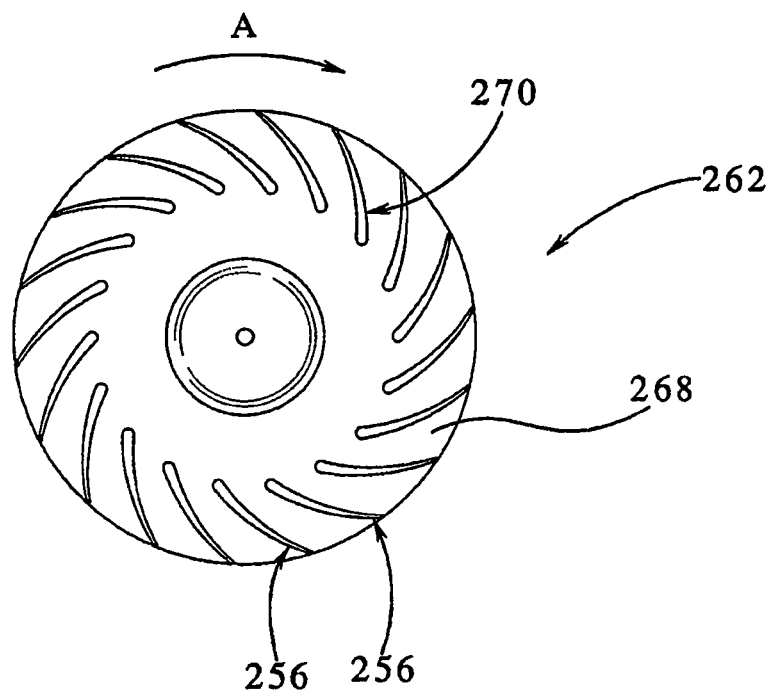
FIG. 2D is a top or plan view of one embodiment of the rotor unit of the air movement device of FIG. 2C.
Figure 2E:
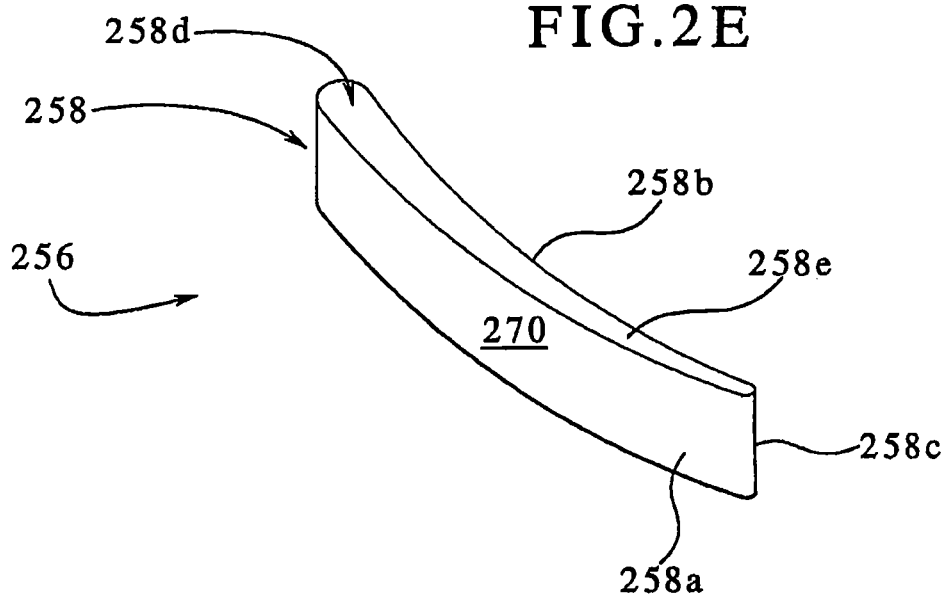
FIG. 2E is a perspective view of one embodiment of an impeller blade of the rotor unit of FIG. 2D illustrating the air foil shape of such impeller blade.
Figure 2F:
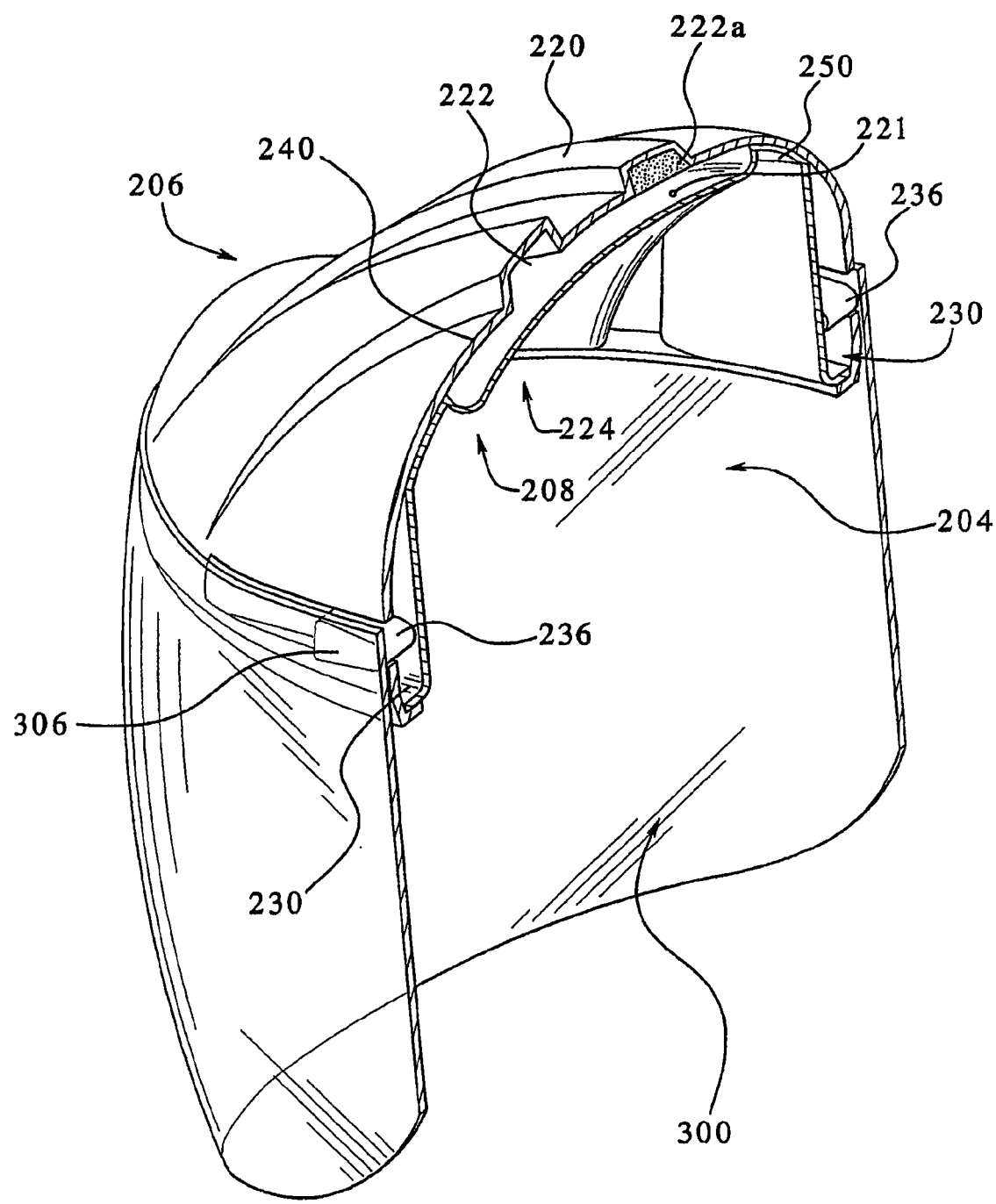
FIG. 2F is a cross-sectional perspective view taken substantially along line 2F-2F of FIG. 1 of one embodiment of the head gear assembly illustrating a central air channel defined by the cooperation of the inner and outer shells.

As illustrated in FIGS. 2 to 2F, the helmet or head gear assembly 200 includes a two-piece helmet, composite shell or shell unit 202, though the shell unit 202 can be constructed from any suitable number of connected pieces or as a single, integral helmet. During normal operation and wear, the shell unit 202 rests forward on the user's head with an interior surface 204 (see FIG. 2A) adjacent to the crown of the head. The shell unit 202 rests above the user's eye and ear level, as illustrated in FIG. 1. This configuration leaves the user's line of eye sight free of obstructions, and it leaves the rear and lateral sides of the user's head open for increased access to air to help cool the head. Typically, the components of the shell unit 202 are manufactured utilizing thermoforming and injection molding techniques, however, depending on the geometry or desired structural characteristics, blow-molding and vacuuming forming techniques may alternately be employed.

A. Shell Unit

As illustrated in FIG. 2, the shell unit 202, in one embodiment, includes: (a) an outer plenum, outer curved wall or an outer shell 206; (b) an inner plenum, inner curved wall or an inner shell 208 connected to the outer shell 206; and (c) an air delivery device, air mover or air movement device 210 which is supported by the inner shell 208.

i. Outer Shell

As illustrated in FIG. 2A, the outer shell 206 has a generally helmet-shaped head piece having a visor portion 212 that aligns and overhangs the user's forehead when the shell unit 202 is worn during normal operation. The outer shell 206 further includes a rear portion 214 formed opposite to and distal from the visor portion 212 that rests adjacent to the back of the user's head when the shell unit 202 is worn during normal operation.

The outer shell 206 further includes a plurality of air intakes 216 forming an air grill or vent within a top or crown portion 218 of the shell unit 202. The plurality of air intakes 216 provide a fluid connection between the air movement device 210 (see FIGS. 2 and 2B) and the atmosphere or other ventilation source. The outer shell 206 of this embodiment is formed or molded to include, or otherwise includes, one or more raised portions or ridges 220 which extend away from the plurality of air intakes 216 towards both the visor portion 212 and the rear portion 214. The ridges 220 serve a variety of functions such as, for example, providing structural reinforcement and rigidity to the outer shell 206.

In one embodiment, the ridges 220 extend substantially vertically away from the an outer shell surface 232 towards the surgical garment 500 when the surgical protective assembly 100 is worn in use. As shown in FIG. 2F, the difference in shape and curvature between the outer shell 206 and the inner shell 208 defines a central air channel or passage 221. Moreover, the interior of the ridges 220 define a plurality of air channels or passages 222 that extend away from the outer shell surface 232 and expand or increase the overall volume of the central air channel 221. The central air channel 221 and/or the air passage 222, in turn, fluidly connect the atmosphere or ventilation source through the plurality of air intakes 216 and the air delivery system 210 to an outlet 224 defined along the periphery of the shell unit 202.

In one embodiment, the air passages 222 are sealed with a conformal material 222a to help further define the central air passage 221 as one continuous space and to encourage laminar air flow between the two shells 206, 208. It will be understood that the differences in the geometry and curvature of the two shells 206, 208 can be altered to modify the shape and size of the central air passage 221 and the air passages 222.

The outer shell 206 further includes a shield engagement assembly 226 integrally formed into the outer shell surface 232. The shield engagement assembly 226 includes an central aligner or central alignment guide 228 formed within, or otherwise connected to, the outer shell surface 232 adjacent to the visor portion 212, and a pair of securing devices, restraints or locks 230 formed along the lateral portions 244 of the outer shell surface 232. In operation, the shield engagement assembly 226 aligns and secures the face shield 300 relative to the shell unit 202 and user's face during normal operation (see FIG. 2 and Section II-B).

The central alignment guide 228 protrudes beyond the outer shell surface 232 and defines a groove or pocket 234. The pocket 234 forms a depression or chamber within the outer shell 206 sized to engage an alignment engager, or tab 302 of the face shield 300 (see FIGS. 3A and 3B). Each of the side securing devices or side locks 230 includes: (a) a restraining wall that defines a restraining slot or locking slot 236; and (b) a restraining engager, or locking tab 238. The locking slot 236 and locking tab 238 combinations are sized and positioned to engage a corresponding locking slot 304 and locking tab 306 combination of the face shield 300.

When the face shield 300 and the head gear assembly 200 are being assembled for use, the alignment tab 302 engages the pocket 234 of the alignment guide 228 in a snap-fit, male-female cooperative arrangement. Specifically, the pocket 234 traps and engages the alignment tab 302 to both vertically and horizontally align the face shield 300 relative to the outer shell 206. Similarly, the locking tab 306 formed on the face shield 300 slideably or removably snaps into the locking slot 236 formed within the outer shell 206, while the locking tab 238 snaps into the corresponding locking slot 304. Thus, each of the elements of the locks 230 engages in a male-female securing relationship with the corresponding elements formed on the face shield 300. These securing male-female relationships serve to removably affix the face shield 300 to the outer shell 206 (and the overall shell unit 202) without the need for an additional joining mechanism such as a snap or adhesive.

ii. Inner Shell

As illustrated in FIGS. 2 and 2B, the inner shell 208 is sized to engage an interior surface 240 of the outer shell 206 (see FIG. 2A). The inner shell 208 includes a ridge or raised wall 242 positioned along its perimeter as defined by the lateral and rear portions 244, 246, respectively, of the inner shell 208. The raised wall 242 extends beyond an inner shell surface 248 and helps define the central air passage 221 and the air passages 222 (see FIG. 2F and Section II-B(iii)). The raised wall 242 includes a plurality of projections, raised portions or ridges 250 aligned and sized to engage the interior portion, e.g., the air channels or passages 222, of the ridges 220. In particular, when the inner shell 208 is aligned within the outer shell 206, the raised wall 242 and the ridges 250 engage the air passages 222 in an interlocking manner. This interlocking arrangement prevents airflow towards the lateral and rear portions 244, 246 of the inner shell 206. The airflow, in turn, is directed along the inner shell surface 248 towards the outlet 224 adjacent to the user's face.

It should be understood that many different configurations of the central air passage 221 and the air passages 222 are possible by altering the shape and configuration of the ridges 220 and the corresponding ridges 250 formed along the raised wall 242. For example, one of the pair of ridges 220 and 250, which is uniquely identified for the sake of clarity as the ridges 220a and 250a, may be designed and manufactured to provide air discharge along the lateral portion 244 of the shell unit 202. In particular, the interior portion of the ridge 220a (which would correspond to an air passages 222a, if such an air passage were visible in these exemplary illustrations) may not be blocked or otherwise engaged by the ridge 250a to allow air flow along the lateral portion 244 of the inner shell 208. In this manner air flow and ventilation can be provided to the user 102 over both the front and sides of the face which may be desirable in some applications.

iii. Air Movement Device

One example of the air movement device 210 that can be incorporated into the head gear assembly 200 is an impeller assembly 252 illustrated in FIG. 2C, though other mechanisms, such as suitable fans and blowers, can be used. The impeller assembly 252 is supported by a mounting wall 254 of the inner shell surface 248 of the inner shell 208.

As illustrated in FIGS. 2C to 2E, the impeller assembly 252, in one embodiment, includes: (a) an electric motor 260 connected to a stationary support or lower frame 255 which, in turn, is supported by the mounting wall 254; and (b) a rotor unit 262 which covers a portion of the frame 255. The lower frame 255 has a motor housing 264 which covers the motor 260 and receives the drive shaft 266 of the motor 260. The rotor unit has: (a) a drive shaft connector 267 which receives and is secured to the drive shaft 266; (b) a blade support frame 268; and (c) a plurality of curvilinear propellers or blades 256 carried by the support frame 268 and arranged about the rotational center line CL. The electric motor 260 is sized to drive the rotor unit 262 at a desired rotational speed. It should be understood that the electric motor 260 may be any type of suitable motor, such as a low-power brush motor sized to be relatively silent and efficient to thereby drive the rotor unit 262.

In one embodiment, the shape or configuration of the blades 256 increases the quietness and efficiency of the air movement device 210, which, in turn, reduces distractions that may be attributed to the overall surgical protective assembly 100, while simultaneously increasing the ventilation performance and overall endurance or operation of the system. As illustrated in FIGS. 2D and 2E, each the curvilinear blades 256 defines a generally semi-circular, crescent or sickle shaped fin configuration arranged to force air, or any other compressible fluid, into the central air passage 221 and the air passages 222 at a designated or variable pressure. As indicated by arrow A, the rotor unit 262, in the illustrated example, moves clockwise, and the curvilinear blades 256 are configured so that the peak region 270 of each blade leads the way, making initial contact with the air or other compressible fluid. The curvilinear blades 256 of the impeller assembly 252 create regions of lower pressure which draws air through the plurality of air intakes 216. The air is then forced and compressed along the leading surfaces or peak regions 270 of the curvilinear blades 256 towards the central air passage 221, the air passages 222 and the outlet 224. In this manner, the air circulates or moves from the rear portion 214 of the helmet or head gear assembly 200 towards the visor portion 212 and the outlet 224. This movement and circulation provides air cooling and ventilating air flow adjacent to the face of the user 102.

As illustrated in FIG. 2E, in one embodiment, each blade 256 is formed into an air foil or tear-shape shape 258 defined by: (a) a leading parabolic wall 258a; and (b) a trailing wall 258b which joins the parabolic wall 258a at an inner vertical edge 258c. The top wall 258d of the blade 256 has a partially triangular shaped-region 258e having a designated vertex where parabolic wall 258a meets the trailing wall 258b. This air foil shape provides a reactive force when rotated relative to the air drawn through the plurality of air intakes 216 which can increase the efficiency and air pressure of the air movement device 210. The increased air pressure results in increased air flow and ventilation through the air passages 222. This air foil shape of the blades 256 can also have advantages in decreasing the level of noise produced by the air movement device 210.

Turning now to FIG. 2F, the central air passage 221 and the air passage 222 form a curved space that roughly corresponds to the general shape defined between the outer shell surface 232 and the inner shell surface 248. It should be understood that the central air channel or passage 221 and the air channels or passages 222 may be expanded or reduced simply by changing the configuration of the ridges 220 and/or the spacing between the raised wall 242 and the inner shell surface 248. Moreover, this sectional view illustrates the locking slots 236 formed along the lateral portions of the outer shell 206. As can clearly be seen, the locking tab 306 extends into the locking slide 236 to secure the face shield 300 to the shell unit 202.

B. Alternate Shell Unit Configuration

Figure 9A:
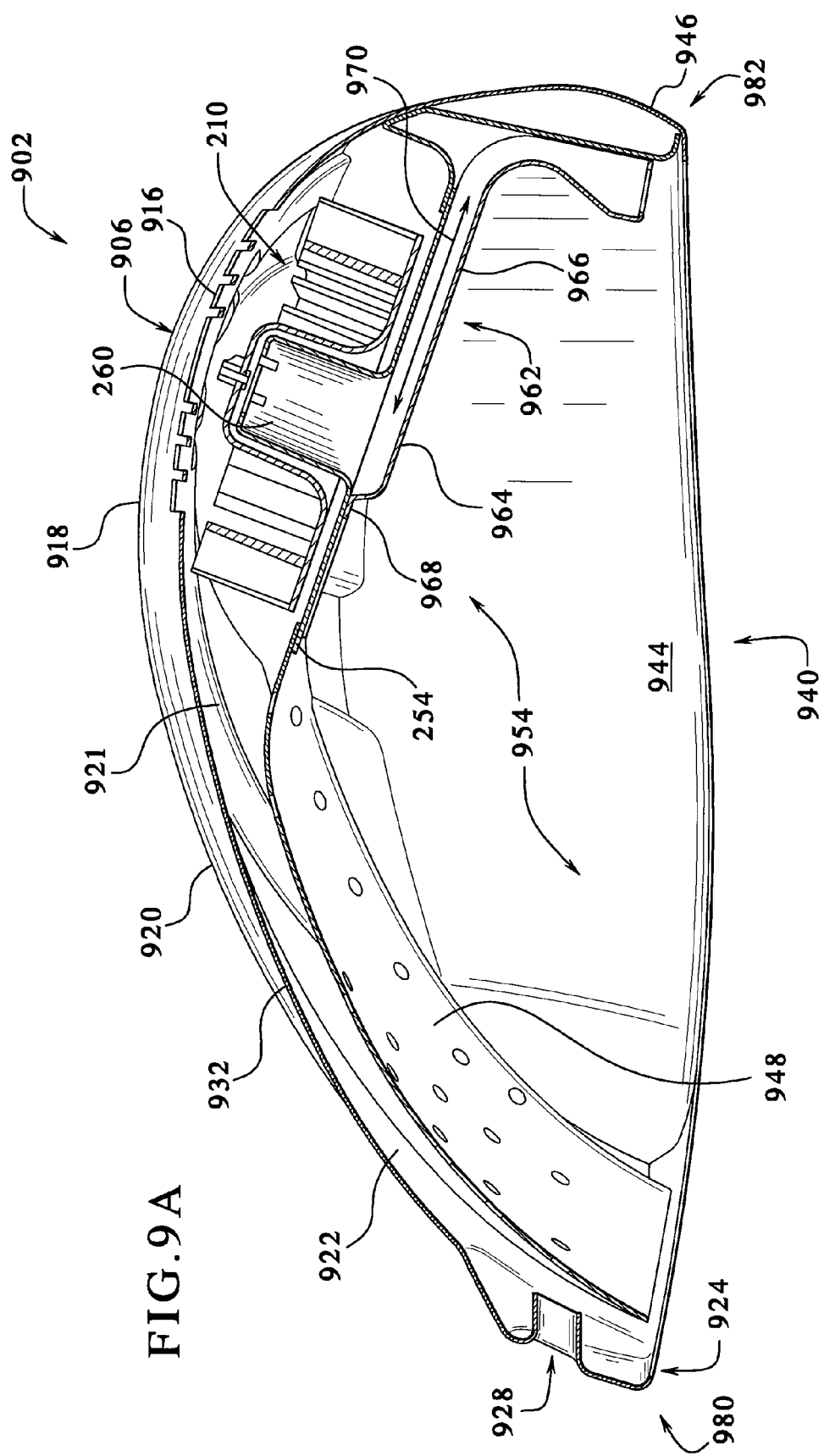
FIG. 9A is a cross-sectional view of the assembled shell unit of FIG. 9 taken substantially along the line 9A-9A and illustrating an air channel fluidly coupling upper and front openings and a plurality of plenum or dome openings defined by the inner shell.

As illustrated in FIGS. 9 and 9A, an alternate embodiment of the shell unit 202 (see FIG. 2) is identified as the shell unit 902. The shell unit 902 includes: (a) an outer curved wall or an outer shell 906; (b) an inner curved wall or an inner shell 908 connected to the outer shell 906. It will be understood that the air movement device 210 (see FIG. 2) may be supported by the inner shell 908 as discussed in connection with the FIGS. 2, 2B and 2C.

i. Outer Shell

As illustrated in FIG. 9, the outer shell 906 has a generally helmet-shaped head piece that includes a visor portion 912 which aligns and overhangs the user's forehead when the shell unit 902 is worn during normal operation. The outer shell 906 further includes a rear portion 914 formed opposite to, and distal from, the visor portion 912 that rests adjacent to the back of the user's head when the shell unit 902 is worn during normal operation.

A top or crown portion 918 of the outer shell 906 includes a plurality of upper openings or air intakes 916 forming an air grill or vent. In the illustrated embodiment, the air intakes 916 are arranged in a plurality of concentric circles. However, it will be understood that the air intakes 916 may be configured with any desired geometry that allows and/or promotes the free flow of air between the environment and the shell unit 902. The outer shell 906 includes a plurality of raised portions or ridges 920 extending away from the air intakes 916 towards both the visor portion 912 and the rear portion 914.

As illustrated in the cross-sectional view of FIG. 9A, the ridges 920 extend substantially vertically away from an outer shell surface 932 of the outer shell 906 and cooperate with the inner shell 904 to define a central air passage or channel 921. Moreover, the interior of the ridges 920 each define an individual air passage or channel 922 that extends away from the outer shell surface 932 and expands or increases the overall volume of the central air channel 921. The central air channel 921 and/or the individual air channels 922 are configured to fluidly connect the atmosphere, via the air intakes 916 and an air movement device such as the air delivery system 210 of FIGS. 2 and 2B, to an outlet 924 defined adjacent to the visor portion 912 along the periphery of the shell unit 902. It will be understood that the differences in the geometry and curvature of the two shells 906 and 908 can be altered to modify the shape and size of the central air passage 921 and/or the air passages 922.

The outer shell 906 may further includes a shield engagement assembly 926 integrally formed into the outer shell surface 932. The shield engagement assembly 926 includes a central aligner or central alignment guide 928 carried by or formed integrally with the outer shell surface 932 adjacent to the visor portion 912, and a pair of securing devices, restraints or locks 930 formed along the lateral portions 944 of the outer shell surface 932. The shield engagement assembly 926 aligns and secures the face shield 300 relative to the shell unit 902 and user's face during normal operation as previously described in Section II-B and illustrated in FIG. 2.

ii. Inner Shell

Figure 10:
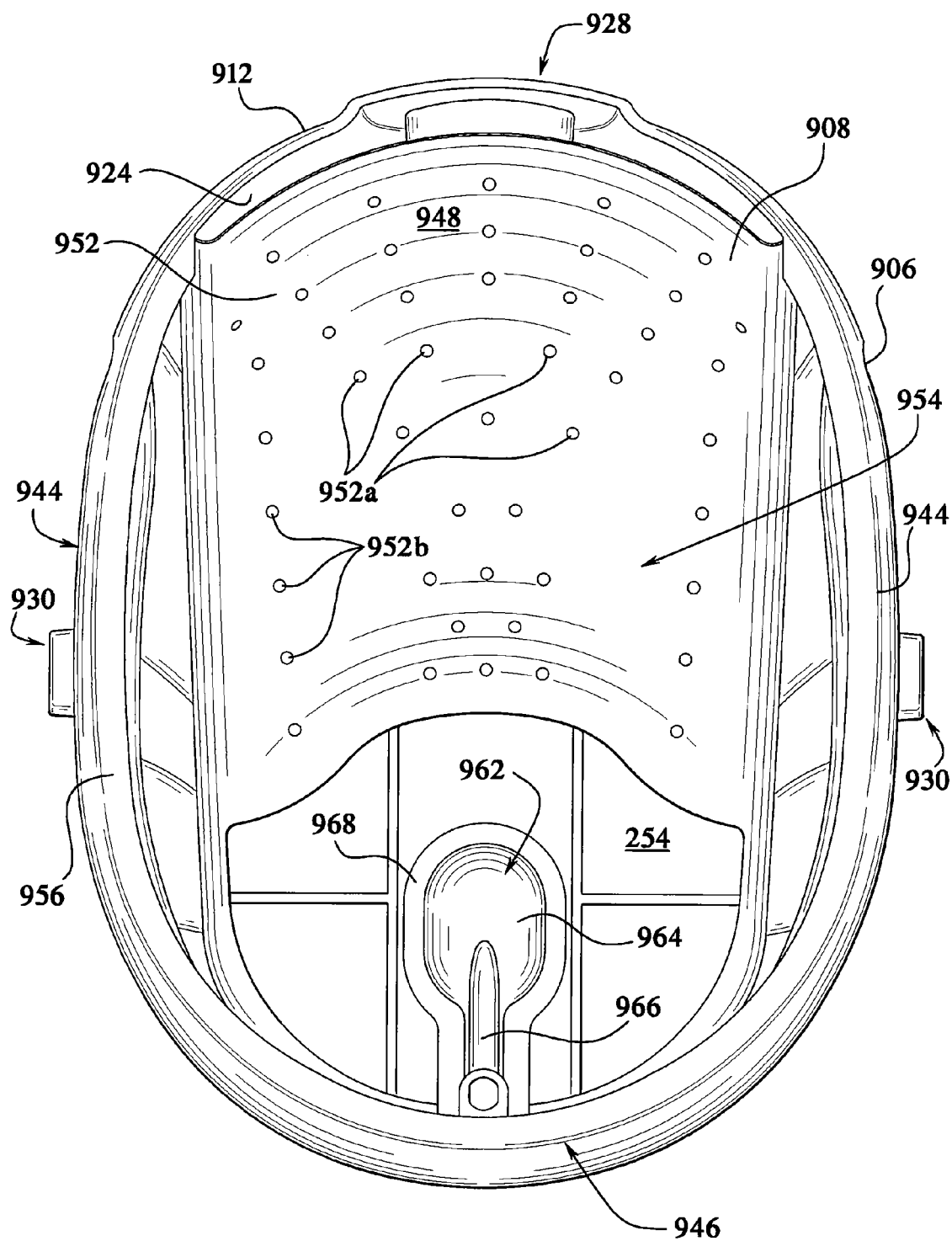
FIG. 10 is a bottom or plan view of the assembled shell unit illustrating the underside of the assembled shell unit of FIG. 9.

FIG. 9 further illustrates the inner shell 908 aligned and sized to engage an interior 940 of the outer shell 906 (see FIG. 10 for a planar assembled view of the inner and outer shells 906, 908). The inner shell 908 includes a ridge or raised wall 942 positioned along and around its perimeter as defined by the lateral and rear portions 944, 946, respectively. The raised wall 942 extends beyond an inner shell surface 948 and helps define the central air channel 921 and the air channels 922 (see FIG. 9A). The raised wall 942 includes a plurality of crenulations or ridges 950 aligned and sized to engage the interior portion, e.g., the air passages or channels 922, of the ridges 920 an interlocking manner. This interlocking arrangement reduces unwanted or undirected airflow towards the lateral and rear portions 944, 946 of the inner shell 906.

The inner shell surface 948, as previously discussed, forms the base or lower portion of the central air channel 921 and the air channels 922. When the shell unit 902 is positioned atop the user's head, the inner shell surface 948 is aligned substantially adjacent and/or parallel to the top of the user's head. The inner shell surface 948 defines a plurality of fluid orifices, holes or dome openings 952. The dome openings 952 are positioned at the dome or arch area of the inner wall 908. The plurality of fluid openings or dome openings 952 provide multiple passages or fluid connections between the central air channel 921, the air channels 922, and an interior 954 of the inner shell surface 948. In operation, the air movement device 210 and the rotor unit 262 draw air from the environment through the air intakes 916, i.e., an opening in the outer shell 906, and into the central air channel 921 and the air channels 922. The air within the central air channel 921 and the air channels 922 is, in turn, distributed, pumped or otherwise provided to the outlet 924, i.e., an opening or output formed between the inner and outer shells 906, 908, and the plurality of dome openings 952 formed in the inner shell surface 948. In this way, air can be provided to both the user's face and the top or crown of the user's head via the outlet 924 and plurality of dome openings 952, respectively. This increased air flow or relatively high volume air flow regulates the climate in the surgical protective assembly 100 to provide an enhanced working environment for the user. In one embodiment, the dome openings 952 substantially increase heat transfer from the crown of the user's head to reduce body heat and perspiration.

In one embodiment, the plurality of dome openings 952 can be evenly and uniformly distributed or arrayed along the inner shell surface 948. Alternatively, the plurality of dome openings 952 can be patterned, arranged or formed along the surface of the inner shell surface 948 to direct or force air to desired areas of the user's head. For example, as shown in FIG. 9, a first portion 952a of the plurality of dome openings 952 forms a substantially triangular shaped pattern or array 952c (as indicated by the dashed line) having a base aligned substantially parallel to the outlet 924 to direct air to forward portions of the user's head. Similarly, a second portion 952b of the plurality of dome openings 952 is linearly aligned adjacent to the raised wall 942 and the lateral portions 944, and directs air flow towards the sides of the user's head.

In one embodiment, the plurality of dome openings 952 can include one or more nozzles or venturis to direct or accelerate air flow towards the crown of the user's head. The nozzles or venturis may be integrally formed as an element of the inner shell surface 948, or may be an additional component or grommet that is carried by or cooperates with one or more of the individual dome openings 952. Depending on the capacity and/or flow rate of the air movement device 210, an overpressure may be created in the central air channel 921 and the air channels 922 to further force or direct air through the fluid openings 952 and the outlet 924.

FIG. 10 illustrates an assembled plan view of the inner and outer shells 906, 908, respectively. In particular, FIG. 10 highlights the interior 954 of the inner shell surface 948 as the inner shell 908 cooperates with the outer shell 906. The outer shell 906 may include a lip or edge 956 arranged to cooperate or carry a corresponding lip or edge 958 formed on the inner shell 908 (see FIG. 9). In one embodiment, these two lips 956, 958 may cooperate in a snap-fit arrangement to secure or hold the inner shell 908 within the outer shell 906. Alternatively, the inner and outer shells 906, 908 may be glued, riveted or otherwise secured together utilizing a variety of mechanical or chemical fastening techniques.

A smooth junction or ridge 960 forms the intersection between the raised wall 942 and the inner shell surface 948. The distance or depth between the raised wall 942 and the inner shell surface 948 determines the size of the smooth junction 960 and the overall volume of the central air channel 921 and air channels 922. For example, as distance between the raised ridge 942 and the inner shell surface 948 also increases, the radius size of the smooth junction 960 increases which, in turn, increases the volume of the central air channel 921 and air channels 922. The smooth junction 960 further reduces the possibility of a sharp and uncomfortable point or edge irritating the user's head and scalp.

FIGS. 9A and 10 further illustrate a motor cover or cord guide 962 that cooperates with the motor housing 254 and the motor 260. The cord guide 962 includes a cover portion 964 sized to enclose and shield the motor 260, and a conduit portion 966 to guide the electrical cord 606 (see FIG. 1) coupled to the motor 260. A lip 968 formed along the periphery of the cover portion 964 and conduit portion 966 provides suitable bonding or coupling surface to which the motor housing 254 and the cord guide 962 may be joined. The motor housing 254 and the cord guide 962 may be, for example, joined using mechanical means such as rivets, tacks or brackets, or may alternatively be joined using a removable adhesive or epoxy. Regardless of the how the components are joined together, the motor housing 254 and the cord guide 962 cooperate to define an open conduit or passage 970 through which the electrical cord 606 may be positioned. This open conduit or passage 970, in turn, guides the electrical cord 606 into a desired position, e.g., hanging down the user's back, to prevents accidental entanglements while the user's is working or operating. Thus, the cord guide 962 increases the usability and ergonomics of the shell unit 902 and the overall head gear assembly 200.

One embodiment includes a method for manufacturing a surgical head gear assembly 902. Referring to FIG. 9A, the method includes the following steps:

(a) coupling an outer wall 906 to an inner wall 908 so that: (i) there is at least one passage 921 between the outer wall 906 and inner wall 908; and (ii) the coupled outer and inner walls 906 and 908 have a front end 980, a rear end 982, and a front opening 924 substantially adjacent to the front end 980 wherein the front opening 924 is fluidly connected to the passage 921;

(b) forming a top or upper opening 916 in the outer wall 906 so that the upper opening 916 is fluidly connected to the passage 921; and (c) forming a plurality of dome openings 952, such as in the form of the orifice array 952c, in the inner wall 908 so that the dome openings 952 are fluidly connected to the passage 921.

This method includes any suitable fabrication process, including, but not limited to, molding, welding, drilling or cutting techniques.

In one embodiment, the orifice array 952c includes a grid or set of relatively small openings 952 which are distributed over a portion of the inner wall 908 in a uniform pattern. The inner wall 908, in one embodiment, includes a permeable surface which enables air to pass through the inner wall 908. The permeable surface can include a mesh structure, a filter or a grid framework.

In one embodiment, the surgical head gear assembly 902 has an air flow parameter which enables the head gear assembly 902 to output a designated flow of air over the user's face and a designated flow of air to the crown of the user's head. This air flow parameter depends upon the following factors, among others: (a) the designated size, shape and location of the front opening 924; (b) the designated size, shape and location of the passage 921; (c) the designated quantity of dome openings 952; and (d) the designated size, shape and location of the dome openings 952. The air flow parameter provides desirable air pressure ratios with respect to the pressure at front opening 924 compared to the pressure at dome openings 952.

In one embodiment, the surgical head gear assembly 902 defines a plurality of suitably sized and placed orifices or openings (not shown) distributed over the entire surface area of the underside or interior of the surgical head gear assembly 902, illustrated in FIG. 10. For example, in one embodiment, the edge 958 of the surgical head gear assembly 902 defines a plurality of orifices or openings (not shown). It should be appreciated that any part of the outer wall 906 and inner wall 908 can include vents, fluid passages or other openings which are suitably sized, positioned and quantified to enable sufficient climate control for the user.

In one embodiment, the surgical head gear assembly or shell unit 902, illustrated in FIGS. 9, 9A and 10, includes all of the parts, components and elements of the head gear assembly 200. It should be understood that any of the embodiments (or portions thereof) described herein can be interchanged or combined to form other suitable embodiments of the surgical protective head gear assembly.

C. Face Shield

Figure 3:
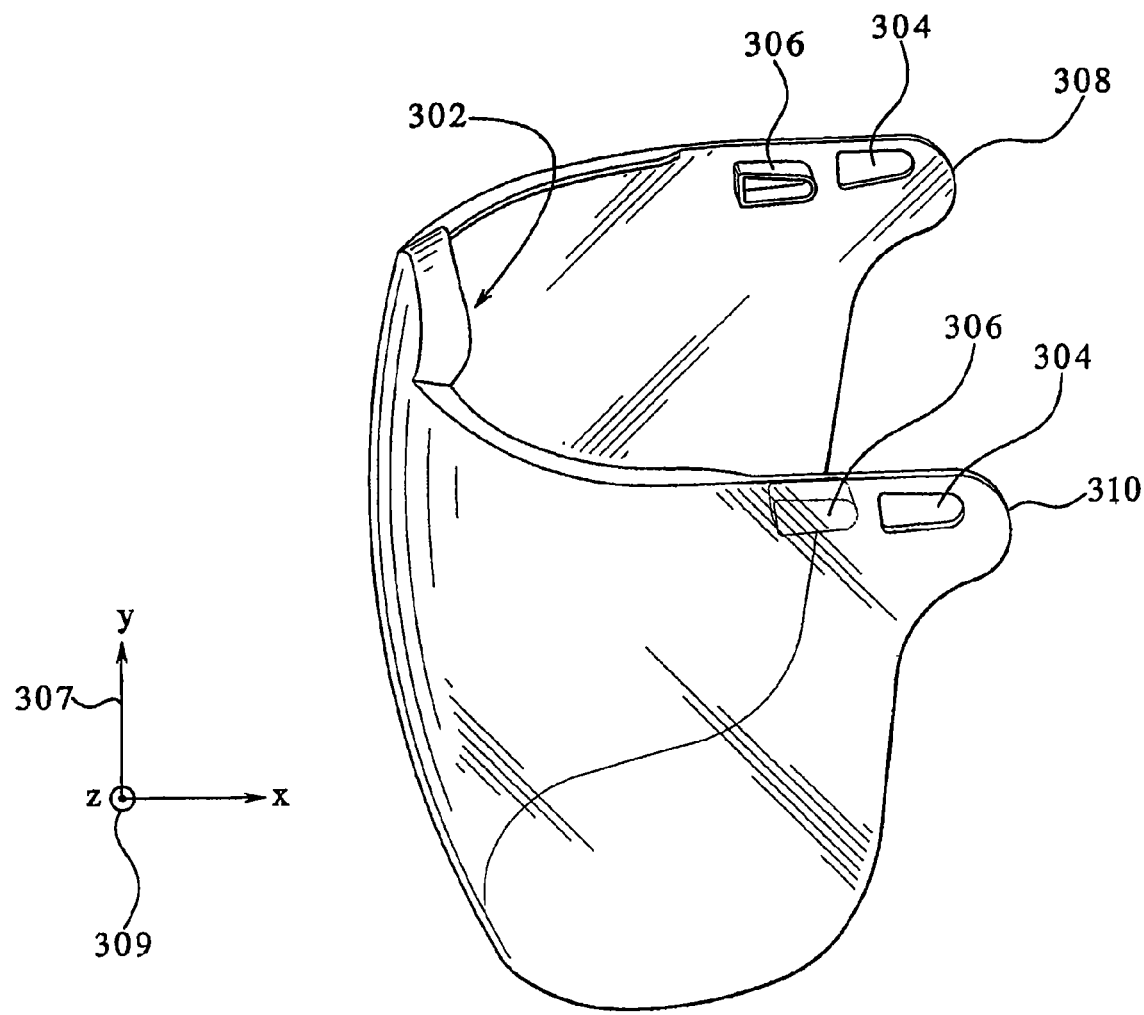
FIG. 3 is a perspective view of one embodiment of the face shield arranged for alignment with the head gear assembly.

Referring to FIG. 3, the face shield 300, in one embodiment, is formed to integrally include the alignment tab 302 and a pair of locking slot and tabs 304 and 306, respectively, formed substantially symmetrically about the centerline CL (see FIG. 3A). The face shield 300 of this embodiment is a bubble or toroidal-shaped shield that curves in two independent and substantially opposite planar directions such that the surface is generated by a closed curve rotating about, but not intersecting or containing, an axis in its own plane. In one embodiment illustrated in FIG. 3, the face shield 300 has a first curvature with respect to the y-axis 307, and the face shield 300 also has a second curvature with respect to the z-axis 309 (as shown relative to the Cartesian indicator set forth in FIG. 3). The curvature of the face shield 300 can be optically corrected by varying the material thickness of the less as a function of curvature in order to reduce visual distortions across the user's field of vision.

The face shield 300 includes a first arm 308 that supports one pair of the locking tab and slot 304 and 306, respectively, and the face shield 300 has a second arm 310 that supports the second pair of locking tabs and slots 304 and 306, respectively. As previously discussed, in order to secure the face shield 300 to the helmet or head gear assembly 200, the alignment tab 302 is inserted into and cooperates with the pocket 234 to center and support the face shield 300 relative to the shell unit 202. Simultaneously, the locking tabs and slots 304 and 306, respectively, on the first and second arms 308 and 310 snap into or otherwise engage the locks 230, 930 on each of the sides of the shell unit 202, 902 in a male-female securing relationship.

As illustrated in FIG. 3A, the surgical garment 500 attaches to the face shield 300 along a bonding area 312 formed around the periphery or edge of the face shield 300. The bonding area 312 designates where the fabric of the surgical garment 500 could be joined, sewn, snapped, connected using a hook and loop fastener such as Velcro® or otherwise removably attached to the face shield 300. In one embodiment, the bonding area 312 does not include the first and second arms 308 and 310 to facilitate alignment and attachment with the shell unit 202, 902. By securing the surgical smock 500 to the bonding area 312, the remaining fabric can be pulled over the user's head to cover the head gear assembly 200 and the shoulders of the user 102 to provide an unobstructed view through the bubble shaped face shield 300.

Figure 3B:
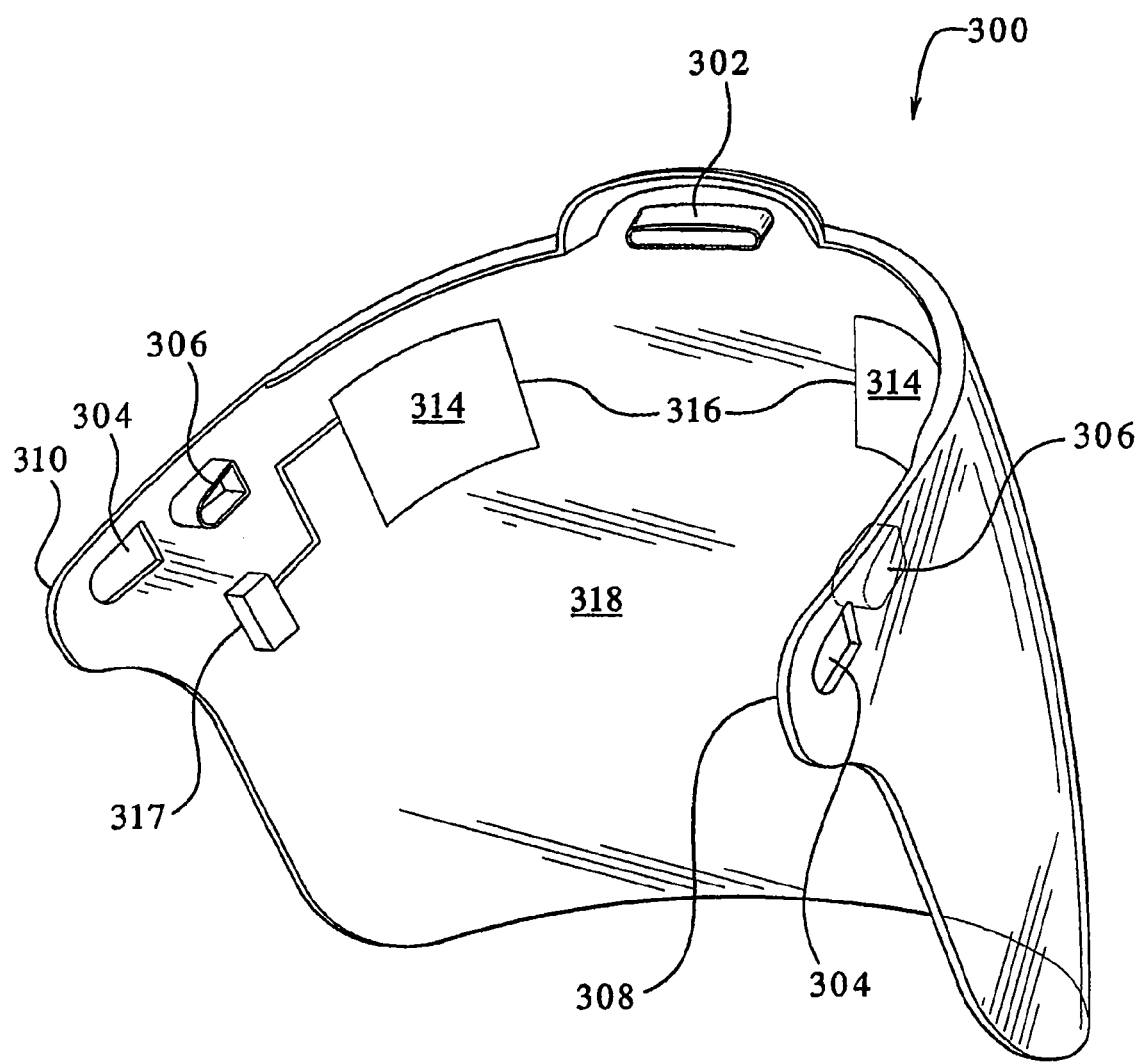
FIG. 3B is an interior perspective view of one embodiment of the face shield, illustrating a display for projecting light or graphical information within the user's field of view on the face shield.

As illustrated in FIG. 3B, the face shield 300 in one embodiment includes a display area 316 on the inner surface 318 of the face shield 300. The display area 316 can be configured to display graphical information 314 or to act as a light source. It should be understood that the display area 316 could be sized and positioned to appear within the user's peripheral vision or may be expanded to encompass the user's entire field of vision depending on the application. The graphical information or graphics 314 displayed may be, for example, text, symbols, a patient's vital statistics, the elapsed time of a procedure or task, an assembly diagram, or information shared through a telepresence system. In this embodiment, display area 316 may be a display screen device (not shown), such as a Liquid Crystal Diode (LCD) screen, which is operatively coupled to a display processor 317. In one embodiment, the light source 314 is retinally controlled through the use of sensors positioned to capture the movement of the user's eyes and interpret the movement through the display processor.

As illustrated in FIG. 3C, the face shield 300, in one embodiment, is adapted to support additional equipment. In particular, the face shield 300 includes a pair of attachment points or mounts 320 formed an outer surface 322 to engage or mount lights, low light vision enhancers, magnifying lenses, or any other desired instrument. It should be understood that the attachment mounts 320 could be any desired structure capable of supporting auxiliary hardware or equipment. For example, the attachment mounts 320 may be threaded holes, clips, posts, indentations, hooks, or any other suitable mounting structure.

Figure 3D:
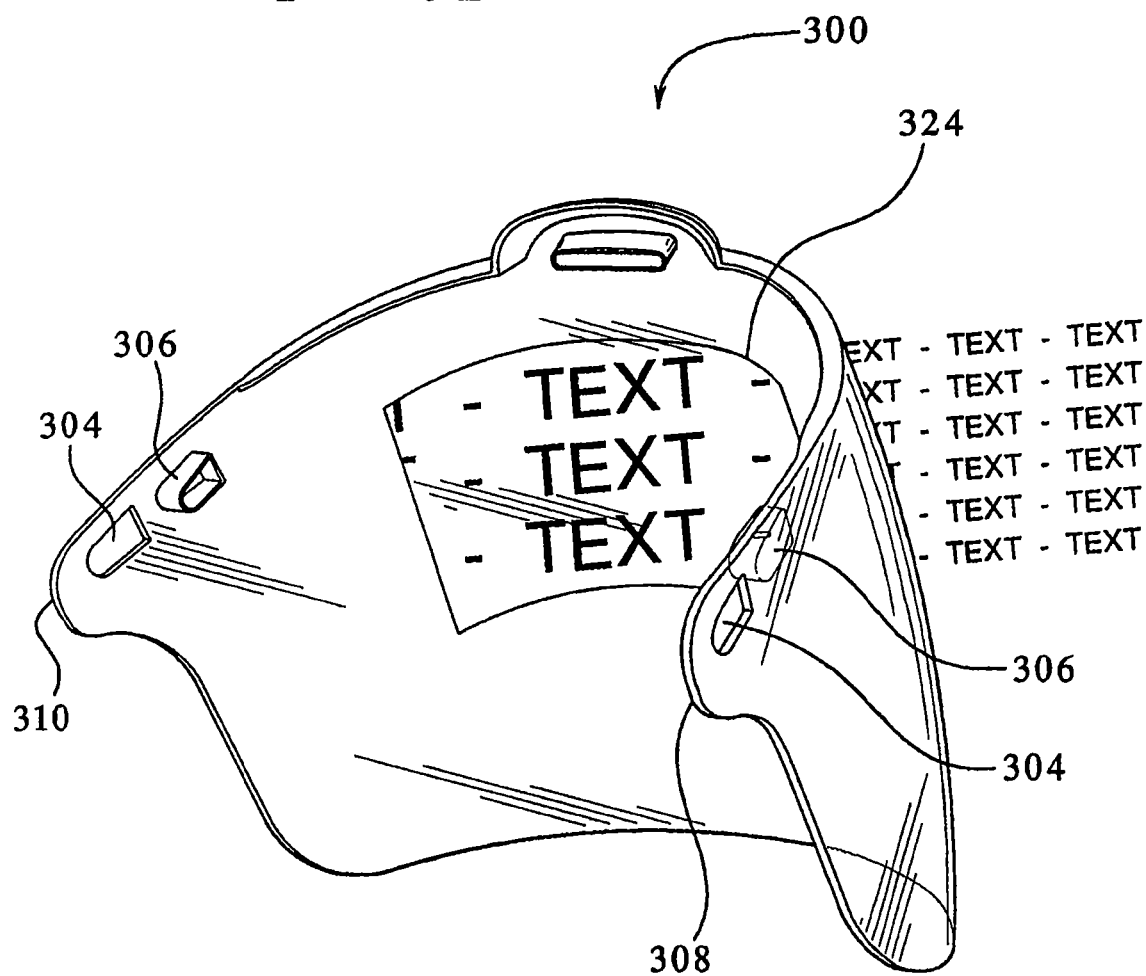
FIG. 3D is an interior perspective view of one embodiment of the face shield having a vision corrective characteristic or device to comply with a user's visual prescription.

As illustrated in FIG. 3D, the face shield 300, in one embodiment, includes a prescription portion or device 324 which includes a vision corrective characteristic adapted to conform with the visual prescription of the user 102. Here, the prescription device 324 includes a vision corrective sheet or enlarged lens which the user can removably attach to the interior surface of the face shield 300. This vision corrective sheet can be disposable and can be attached to the face shield 300 through static forces, adhesives or any other suitable fashion. Alternatively, the composition of the face shield 300 can include a vision corrective property adapted specifically for the user 102. In either case, this embodiment of the face shield 300 can eliminate the need to wear glasses, goggles and contacts while performing a task.

Figure 3E:
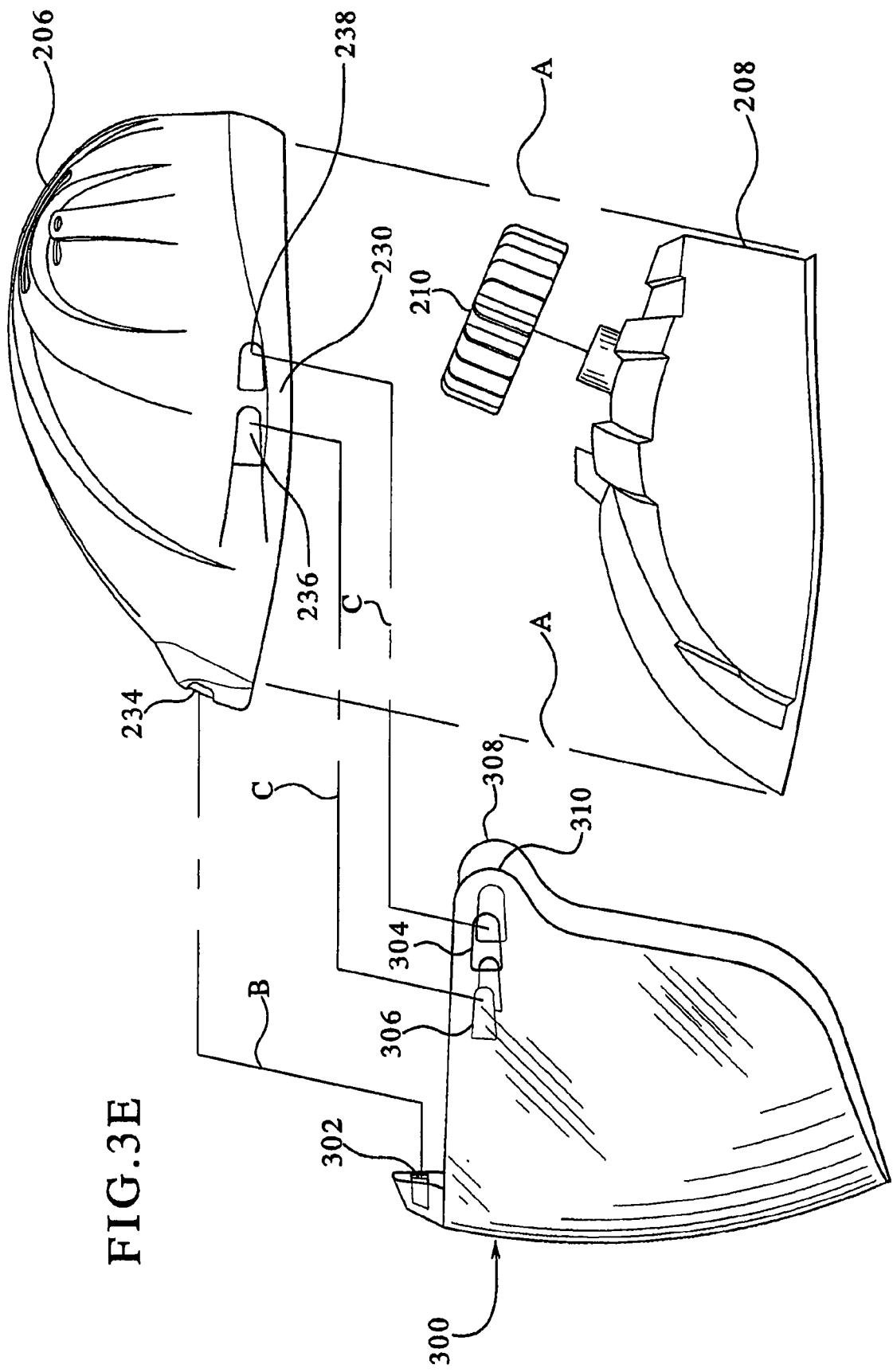
FIG. 3E is an exploded side elevation view of one embodiment of the head gear assembly aligned for cooperation with the face shield of FIG. 3.

As illustrated in FIG. 3E, the outer shell or outer wall 206 of the shell unit 202 aligns with the inner shell or inner wall 208 and the impeller 252 along the lines indicated by the reference indicator A. Similarly, the alignment tab 302 of the face shield 300 aligns with the pocket 234 formed within the outer shell 206 along the line indicated by the reference indicator B. The locking slot 304 and locking tab 306 align and engage the locking tab 238 and locking slot 236 formed along the lateral portion of the outer shell 206 as indicated by the lines designated by the reference indicator C. These subsystems of the surgical protective assembly 100 can be interconnected and joined to formed a single integrated unit that can be worn on a user's head. It will be understood that the systems and elements of the face shield 300 can cooperate with, or otherwise mount to, either the shell unit 202 or the shell unit 902 in manners similar to those discussed above.

D. Adjustable Head Securing Assembly

Figure 4:
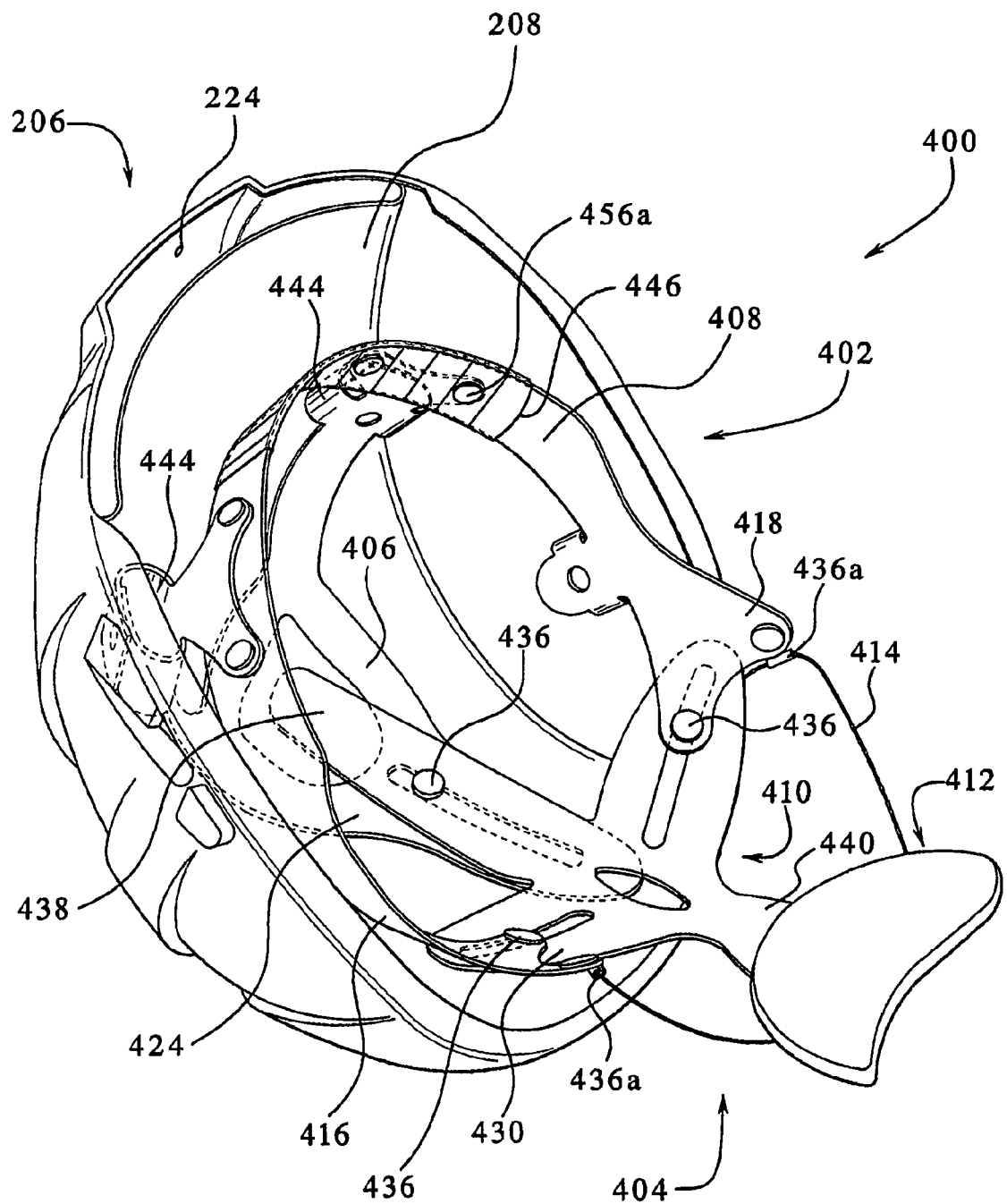
FIG. 4 is a perspective view of one embodiment of the adjustable head securing assembly cooperating with the surgical head gear assembly of FIG. 2A.
Figure 4B:
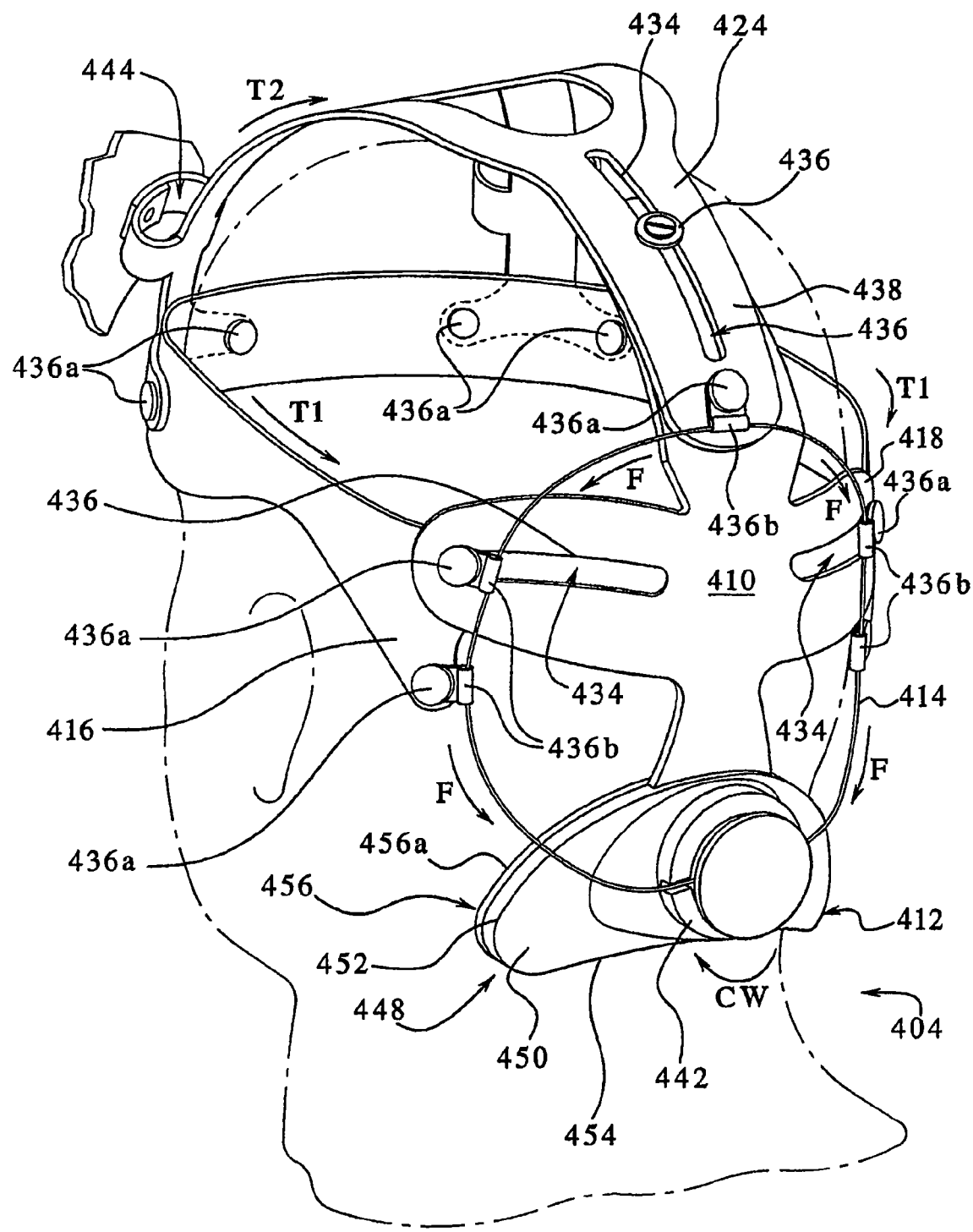
FIG. 4B is another rear perspective view of one embodiment of the adjustable head securing assembly, illustrating the operation of one embodiment of the tensioning assembly.

Referring to FIGS. 4, 4A and 4B, the adjustable head securing assembly 400 includes: (a) a head support assembly 402 coupled to the shell unit 202 through the biasing members, cushions or deformable connectors 444; and (b) a tensioning assembly 404 which is coupled to the head support assembly 402. The head support assembly 402 includes: (a) an upper support band 406 which transmits the weight of the shell unit 202 to the user's head; and (b) a forehead or lower band 408 which stabilizes the shell unit 202 with respect the front and sides of the user's head.

The tensioning assembly 404 includes: (a) a multi-arm tensioning band 410 which is slidably coupled to the lower band 408; (b) a tensioning device 412 which enables users to adjust the degree of tension; and (c) a tensioning band, flexible force transmitter or cord 414 arranged to moveably couple the multi-arm tensioning band 410 and the tensioning device 412 to the head support assembly 402.

i. Head Support Assembly

The head support assembly 402, as illustrated, is intended to be worn with the upper support band 406 resting adjacent to the crown of the user's head and the lower band 408 resting adjacent to the user's forehead and temple area. It should be understood that the head support assembly 402 may be secured within the shell unit 202 in a variety of manners. For instance, the head support assembly 402 may be secured directly to the inner shell 208 to allow modular assembly of each component within the head gear assembly 200. Alternatively, the head support assembly 402 may be directly secured to an inner surface of the outer shell 206 thereby leaving the inner shell 208 unencumbered.

As illustrated in the embodiment of FIGS. 4, 4A and 4B, when the head securing assembly 400 and head gear assembly 200 are cooperating in use, the lower band 408 wraps around the user's head such that a first end 416 and a second end 418 extend away from the visor portion 212. The upper support band 406 of this embodiment is a Y-shaped band that extends along the top the user's head and is aligned front to back within the shell unit 202. The Y-shaped upper support band 406 includes a first support arm 420, a second support arm 422 and an adjustment arm 424.

When assembled, the first and second support arms 420 and 422, respectively, are attached or rivet to the lower band 408 adjacent to the user's temples. Low profile rivets or other suitable fasteners 436a can be used to attach the components of the head securing apparatus 400 to reduce the likelihood of poking, creating pressure points or other user sources discomfort. In addition, a soft or deformable comfort band 446 can be attached to the components to cushion the user and act as a perspiration absorber.

Each of the first and second support arms 420 and 422, respectively, includes a first and second flexible sub-arm 426 and 428, respectively. For the sake of clarity, the following description will focus on the first support arm 420 and the first and second flexible sub-arms 426 and 428 connected thereto. However, it should be noted that the second support arm 422 includes identical components and operates in a similar manner. The flexible sub-arms 426 and 428 of this embodiment extend substantially perpendicular from the support arm 420. In other words, if the first support arm 420 were viewed in a plan view, the first flexible sub-arm 426 and the second flexible sub-arm 428 would cooperate to form a roughly cross shape.

In one embodiment, the deformable connectors 444 (see FIGS. 4 and 4B) are formed by folding or bending the first flexible sub-arm 426 towards the second flexible sub-arm 428 such that the distal ends 426a and 428a overlap, forming a loop structure. This flexible loop structure, in turn, is affixed to the shell unit 202 to allow the support band 406 and lower band 408 to flex, shift and adjust for comfort relative to the composite shell.

Each of the deformable connectors 444 functions as a cushion to distribute the force and weight that is conveyed through the shell unit 202 and the head securing assembly 400 to the user's head. In this way, the head support assembly 402 provides for additional freedom of movement relative to the shell unit 202 thereby increasing the wearability and user comfort of the helmet or head gear assembly 200. It should be appreciated that the lower band 408 can be similarly attached within the shell unit 202 to provide lateral cushioning of the head support assembly, or may, in other embodiments, directly attach to the outer shell 206 and/or inner shell 208.

ii. Tensioning Assembly

In further description of the tensioning assembly 404, the multi-arm tensioning band 410 includes a left adjustable arm 430 and a right adjustable arm 432. The left and right adjustable arms 430, 432 each have a pair of inner slot walls 434a, 434b which define a slot 434 aligned along their respective lengths. The slots 434 are sized to slideably or movably accept a slot follower or cylindrical follower 436 secured within the first and second ends 416 and 418, respectively, of the lower band 408. Stated another way, the left and right adjustable arms 430 and 432 can be flexed and wrapped around the rear of the user's head such that the cylindrical followers 436 secured within the first and second ends 416, 418 fit within the slots 434. This sliding relationship allows the multi-arm tensioning band 410 to be shifted relative to the lower band 408.

In addition, the multi-arm tensioning band 410 includes an upper arm 438 which is movably coupled to the sub-arm 424 of the upper support band 406. Here, a fastener 436a is positioned adjacent to the slot 434 and the cylindrical follower 436 is secured within the slot 434 of the sub-arm 424. Moreover, the fastener 436a is connected to the upper arm 438 of the multi-arm tensioning band 410 so that the cylindrical follower 436a may traverse along the slot 434. Accordingly, the position of the upper arm 438 and the sub-arm 424 is adjustable by the user. This adjustment function enables the tensioning assembly 404 to be adjusted and shifted relative to the head support assembly 402, and this function also facilitates conformity of the head securing assembly 400 to the user's head.

The tensioning device or tensioner 412 attaches, in this embodiment, to the multi-arm tensioning band 410 through a flexible mounting arm 440. The tensioning device 412 includes a hand control, knob or rotary ratchet 442 that is coupled to the tensioning cord 414. The tensioning cord 414 is connected to the first and second ends 416 and 418 of the lower band 408 and the adjustment arm 424 of the head support assembly 402 to allow these components to contract and release in a unified manner. Specifically, the tensioning cord 414 is connected to sliding fasteners 436b which, in turn, may be connected to the followers 436 and/or fasteners 436a.

By rotating the rotary ratchet 442 the tensioning cord 414 can be extended or retracted (depending on the direction of rotation) to increase or decrease the tension applied to the head support assembly 402. An increase in the tension transmitted through the tensioning cord 414, pulls or forces the first and second ends 416, 418 to slide along the slot 434 thereby increasing the tension along the entire lower band 408. Similarly, an increase in the tension along the tensioning cord 414 forces the adjustment arm 424 to slide along the slot 434, relative to the fastener 436a and the follower 436 secured within the fixed arm 438, thereby increasing the tension and fit of the support band 406.

As illustrated in FIG. 4B, the tensioning assembly 404 moves as the force transmitted through the tensioning cord 414 increases. In particular, clockwise rotation of the rotary ratchet 442 as indicated by the arrow CW causes the tensioning cord 414 to retract as indicated by the forced arrows F. Retraction of the tensioning cord 414 further causes the first and second ends 416, 418 of the lower band 408 to retract around the user's head and temples as indicated by the arrows T1. Simultaneously, retracting tensioning cord 414 pulls the adjustment arm 424 relative to the fixed arm 438 to tighten the overall fit of the support band 406 relative to the user's head as indicated by the arrow T2.

As illustrated in FIGS. 4A and 4B, the tensioner 412 also includes a neck or lower head engager or lower head support 448 which includes: (a) a housing 450 that supports the rotary ratchet 442; (b) a rounded upper wall 452; (c) a substantially straight lower wall 454 located opposite the upper wall 452; and (d) a head engagement surface 456 which includes a relatively soft comfort band 456a. The lower head support 448 transfers some of the weight of the shell unit 202, air movement device 210, face shield 300 and surgical garment 500 to the based of the user's skull or lower portion of the neck region. This transfer of weight reduces the leverage effect of the weight on the user's upper head, which, in turn, reduces the fatigue on the user's neck and upper body muscles.

In one embodiment, the head support assembly 402, as coupled to tensioning assembly 404, provides at least three degrees of freedom for making two types of adjustments. The first type of adjustment, tension adjustment, involves increasing and decreasing the tension of the head securing assembly 400 on the user's head. The second type of adjustment, head shape adjustment, involves enabling the lengths of the different band arms to change, through the follower and slot process described above, to conform (or substantially conform) to the unique shape of the user's head. Accordingly, the head securing assembly 400 provides enhanced comfort and adjustment functions for users.

III. Surgical Garment

Figure 5:
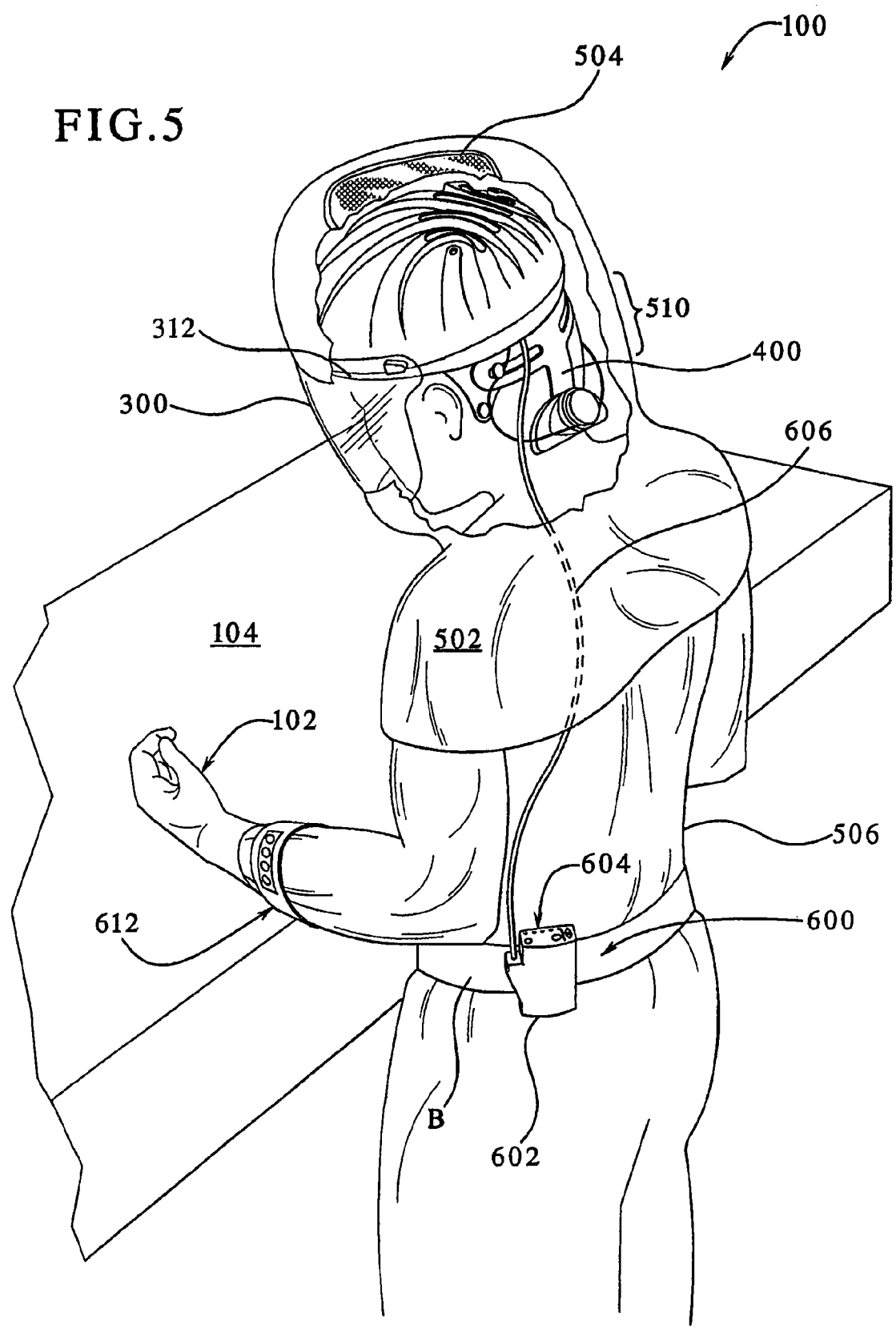
FIG. 5 is a rear perspective view of the surgical personal protective system or assembly shown in FIG. 1, illustrating a user wearing a belt-mounted air control device or controller electrically coupled to the head gear assembly with an electrical cord.

Referring back to FIG. 1, the surgical garment 500, in one embodiment, includes a body suit or full length surgical garment 508 having an upper body cover or hood 502. The hood 502 can be integral with the lower portion of the garment 500, as illustrated in FIG. 1. Here, the surgical body suit 508 provides additional frontal protection to the user 102 from debris and containments which may be encountered from the working surface 104. Alternatively, the hood 502 can be separately used in conjunction with any suitable surgical lower body clothing set or scrubs 506, as illustrated in FIG. 5.

In either embodiment, the surgical hood 502 covers both the hear gear assembly 200 and the adjustable head securing assembly 400 while covering the user's shoulders and chest. As discussed in connection with FIG. 3A, the surgical hood 502 can be attached to the face shield 300 along the bonding area 312. The surgical hood 502 will typically be turned inside out as the face shield 300 is aligned and affixed to the head gear assembly 200 in the manner described. Upon assembly and alignment of the face shield 300 to the head gear 200, the surgical smock 502 will typically be pulled over the user's head to cover the exposed components of the head gear assembly 200 and the adjustable head securing assembly 400.

The surgical hood 502 may be manufactured from any suitable surgical fabric to help repel water, debris and other containments such as blood born pathogens, and viruses. One non-limiting example of a suitable surgical fabric may be the fabric which is commercially known as ProVent® 3000 and is sold by Kappler, Inc. headquartered in Guntersville, Ala. ProVent® 3000 is a relatively lightweight fabric with relatively soft, draping characteristics that utilizes a microporous film to allow gas to pass through the fabric. This ProVent® 3000 fabric meets or substantially meets the American Society for Testing and Materials (ASTM) F1670-98 standard for blood penetration resistance. The surgical fabric can be a multilayer fabric which meets or substantially meets the ASTM F1671-97B standard for viral penetration resistance. In one non-limiting example of the fabric of the hood 502, the fabric has a pore size in the approximate range of 0.08 to 0.15 microns. It should be appreciated, however, that the fabric can have any suitable pore size or structure.

The surgical hood 502 may further act as filter to prevent debris and containments from entering the surgical protective assembly 100 through the plurality of air intakes 216 and the impeller 252. Specifically, the surgical garment 500 and the surgical hood 502 can include a primary filter 510 (see FIG. 1) positioned adjacent to the tensioning device 412 or at any other position towards the rear of the user's head and the adjustable head securing apparatus 400. The location of the primary filter 510 provides increased filtering for air or other fluids entering and/or exiting the surgical protective assembly 100.

A secondary filter 504 may be incorporated into the surgical garment 500 and surgical hood 502 adjacent to the head gear assembly 200 to provide additional filtering (see also FIG. 3A) of the air entering through the plurality of air intakes 216. The secondary filter 504 may be a multilayer filter to trap and filter particles of varying sizes. Moreover, the secondary filter 504 can be manufactured in a variety of sizes to cover the entire crown of the use's head (as shown in FIG. 5) or to cover the plurality of air inlets 216. Similarly, the primary filter 510 can be expanded to include the fabric of the entire surgical garment 500 and surgical hood 502, or any portion thereof. In one operation example, the air flow generated by the air movement device 210 enters the surgical protective assembly 100 through the secondary filter 504 and the plurality of air intakes 216, flows over the user's face via the outlet 224 and exits the surgical protective assembly 100 through the primary filter 100.

IV. Control Device

Figure 6:
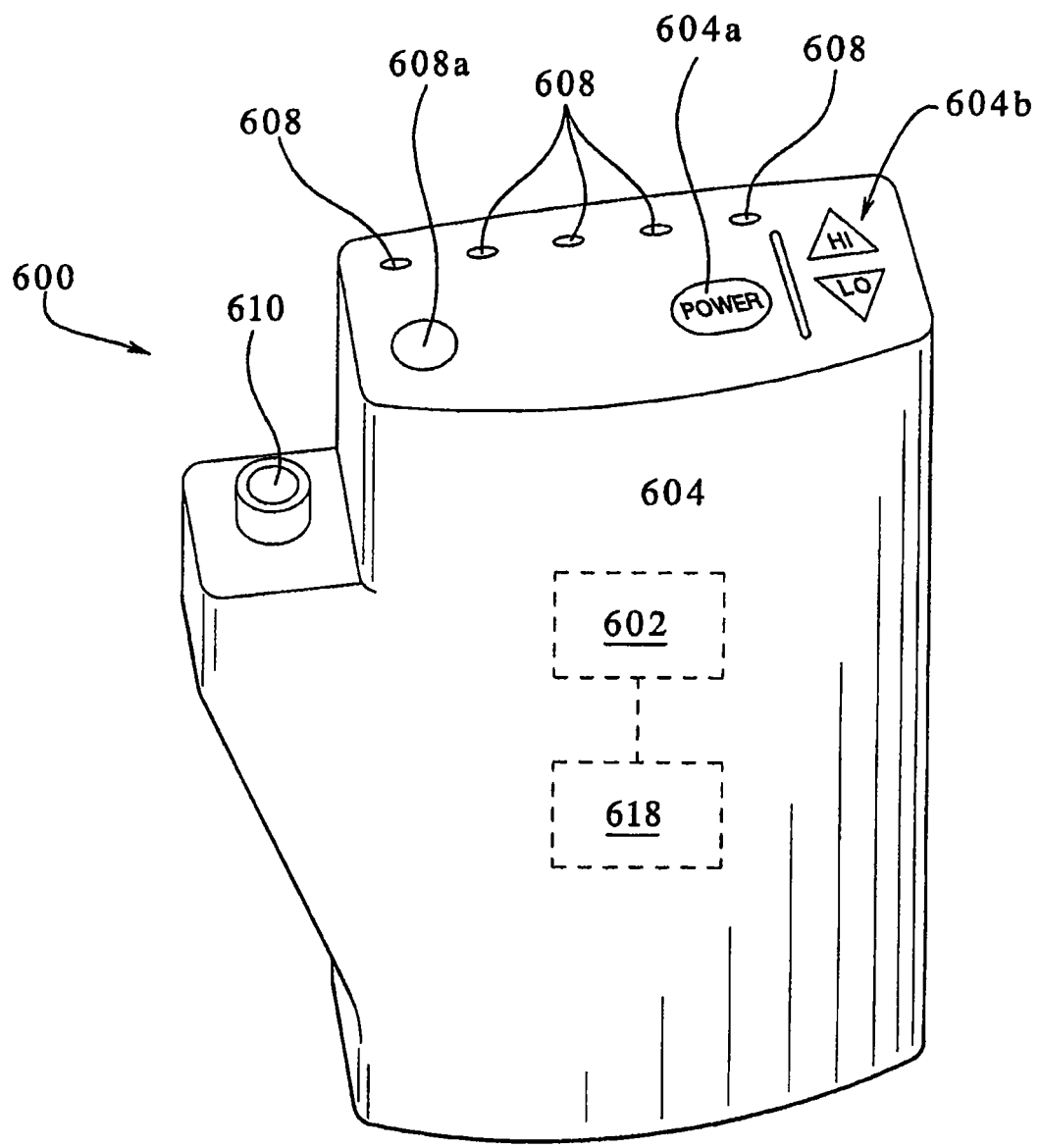
FIG. 6 is a perspective view of the a control device or controller of FIG. 5 with the electrical cord removed.

As illustrated in FIGS. 1, 5 and 6, the control device 600 includes a controller or processor 602 having a power control and speed control input device 604 and one or more rechargeable battery cells 618. The processor 602 is electronically coupled to the head gear assembly 200, and more specifically to the impeller 252 and motor 260, though an electrical cord 606.

In operation, the user engages or actuates the power switch 604a to provide electrical or motive power to the impeller 252. The user may further increase or decrease the motive power (i.e., the electrical energy provided by the battery), using a power regulator or speed control input device 604b. In this way, the speed of the impeller 252 may be controlled simply by changing the amount of power provided from the battery through the power switch 604a, and the speed control 604b is communicatively connected to the impeller 252 through the electrical cord 606.

With continued reference to FIG. 6, the control device 600 includes a plurality of charge level indicators 608 arranged to provide a graphical representation or output of the amount of the power remaining within the battery 618. The control device 600 also includes an output actuator 608a which, when actuated by a user, activates the charge level indicators 608. Alternatively, the charge level indicators 608 may remain active indefinitely or for a designated amount of time. The control device 600 further includes an electrical connector or socket 610 sized to accept a plug (not shown) adapted to be formed or connected to the electrical cord 606. In addition, the control device 600, in one embodiment, includes a mount device or clip (not shown) which enables the user to attach the controller 602 to the user's belt, waist band or pocket (see FIGS. 1 and 5). It should be understood that the controller 602 may be worn by the user 102 by employing the belt clip, a holster (not shown) or any other suitable body attachment device.

Alternatively, the control device 600 may include a battery 618 and a transmitter (not shown) communicatively connected to a receiver 612 which may be worn, for example, on the wrist, or incorporated within the head gear assembly 200 as illustrated in FIG. 5. Information may be communicated between the receiver 612 and the controller 602 using any known communication protocol to establish a personal area network. In this way, information may be displayed on the receiver 612, or on the interior of the face shield 300, as previously discussed. Moreover, the control device 600 and the battery cells 618 may include an automatic shut-off feature that disables or powers down the batteries and controller 602 if the electrical cord 606 is intentionally or inadvertently removed from the socket 610.

V. Charge Device

Figure 7:
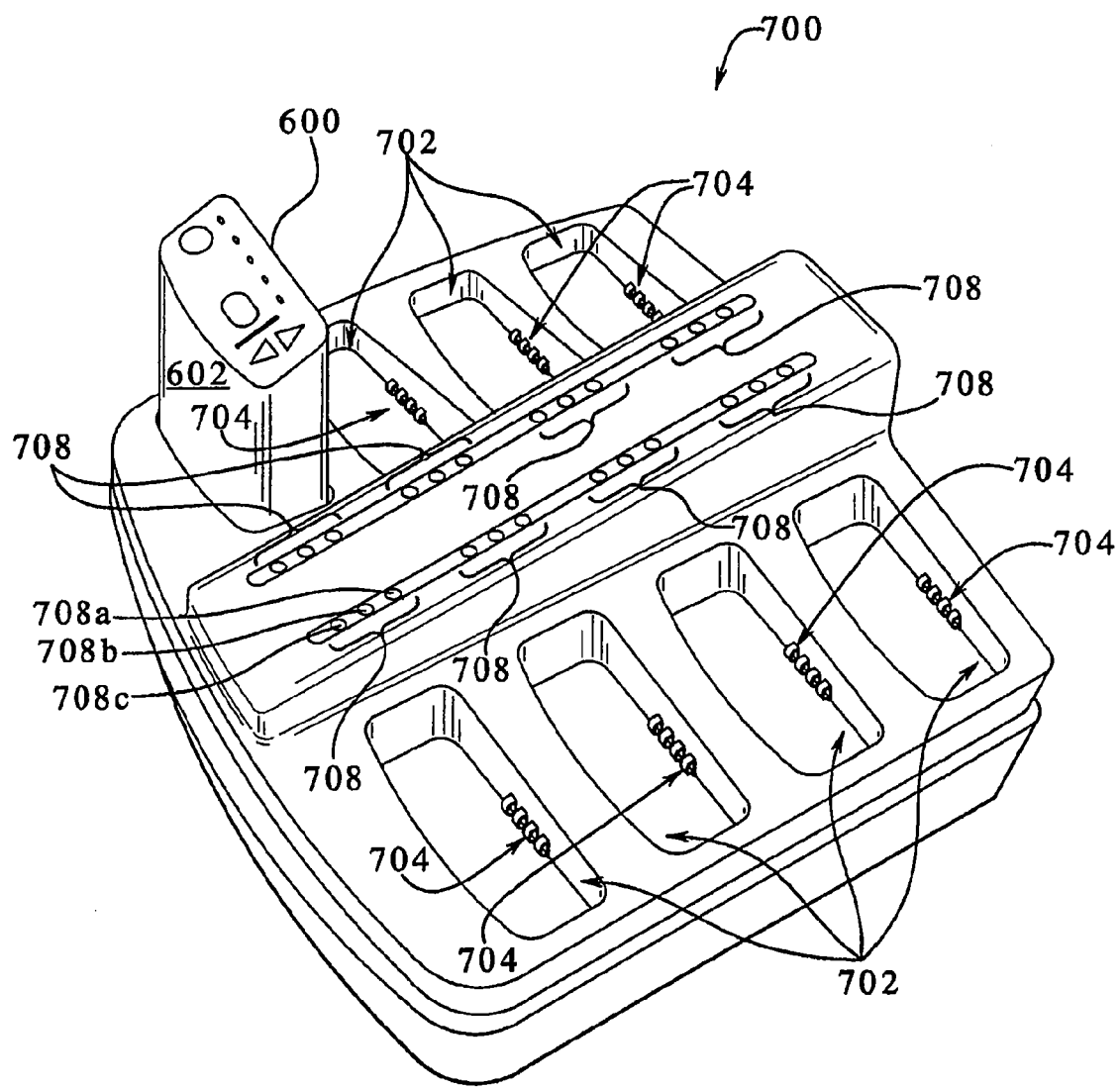
FIG. 7 is a perspective view of one embodiment of the battery charger, illustrating a control device or controller connected within a battery charge station.
Figure 8:
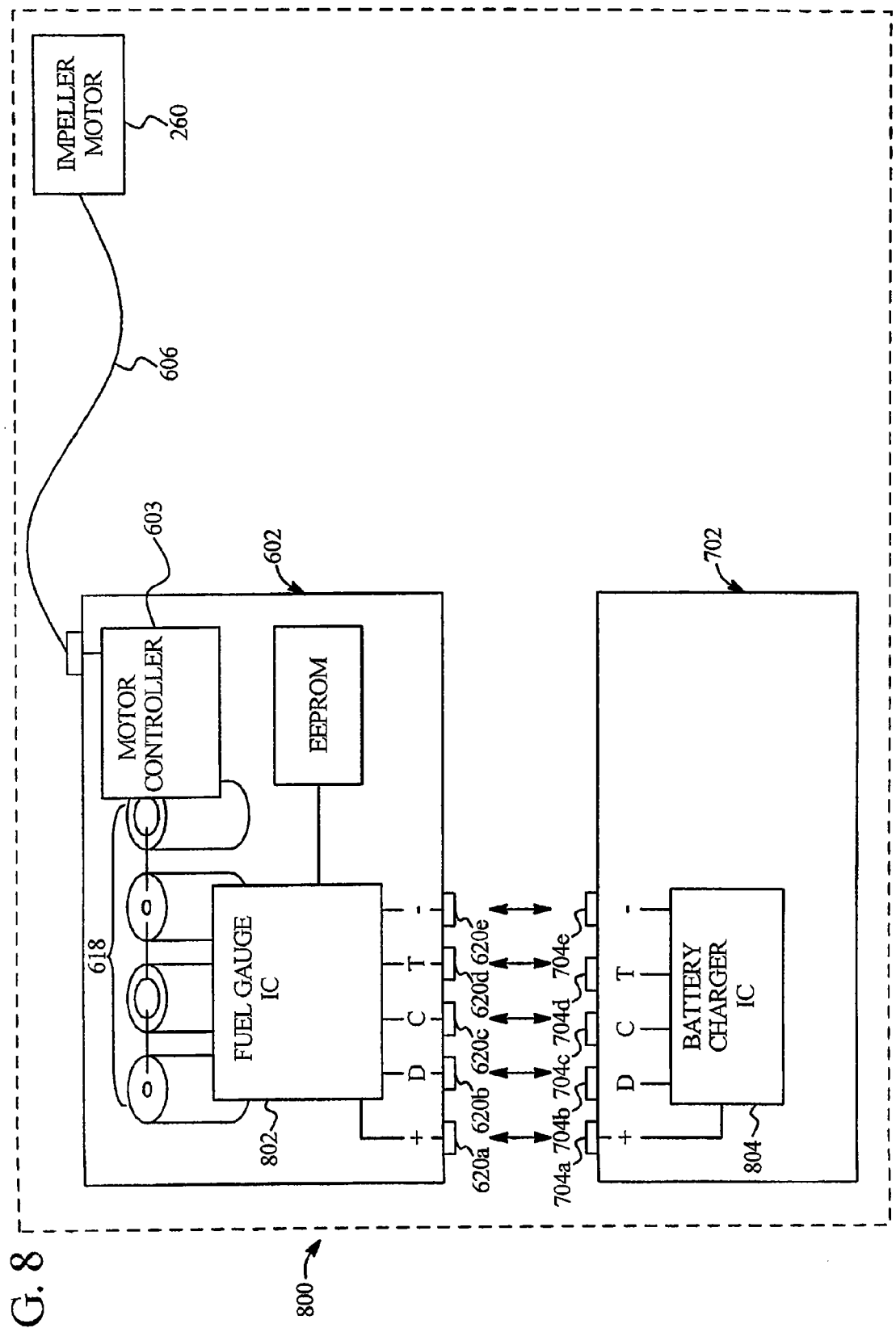
FIG. 8 is a schematic diagram of one embodiment of the electronic configuration of the control device and the battery charge device of FIG. 7.

Referring to FIGS. 7 and 8, the charge device 700 has a plurality of charge stations or bays 702 arranged to accept one or more of the control device 600. Each of the bays 702 includes a plurality of electrical contacts 704 arranged to cooperate with contacts 710 and 710a formed on the control device 600. The charge device 700 further includes a plurality of charge indicators or lights 708 adjacent to each one of the bays 702. The lights 708 are arranged to display the charge status of each of the control devices 600 lodged in the charge device 700. In the illustrated example, each bay 702 is associated with three indicators 708a, 708b and 708c. Indicator 708a produces a red light when one of the control devices 600 is defective, which may occur, for example, if its battery cell is damaged. Indicator 708b produces an orange or yellow light when one of the control devices 600 has an insufficient level of change and is in the process of being recharged. Indicator 708c produces a green light when one of the control devices 600 is charged and ready for use. In this fashion, the indicator lights 708 indicate to the users 102 whether the controllers 602 have a status of "error," "charging" or "fully charged." While the electrical contacts 704 are shown in this embodiment, it should be appreciated that the controllers 602 may be magnetically coupled to the charge device 700 through a magnetic circuit in order to inductively charge the battery.

As previously discussed, the control device 600 and the charge device 700 cooperate to charge and recharge the battery 618 to enable repeated performance of the impeller 252 motor. In one embodiment, the control device 600 and the charge device 618 have the electronic configuration 800 illustrated in FIG. 8. One example of a motor 260 that may be used to drive the impeller 252 is a three-phase sensorless, brush direct current (DC) having an operational voltage of ten and four-tenths VDC. The processor 602, communicatively connected to the impeller motor 260 through the electrical cord 612, can include an application-specific integrated circuit (ASIC), or motor controller 603 processor for controlling the motor 260. In particular, the controller 603 can include a pair of resistors capable of controlling the speed of the motor 260. Alternatively, the controller 603 can control the motor using pulse-width modulation (PWM) for low noise applications such that a sine wave PWM-mode generates motor current with relatively low distortion and therefore relatively low audio noise. An external control voltage can be connected to the motor controller 603 for controlling the duty cycle, wherein the duty cycle can also be controlled by using an integrated phase-locked loop (PLL) circuit for speed control.

In one embodiment, the battery can include one or more rechargeable cylindrical lithium ion cells (generally indicated as the battery 618) connected in series and communicatively connected to a fuel gauge integrated circuit 802 (IC) that conforms to the smart battery industry standard. The smart battery standard governs and controls the charge and discharge of the battery to enhance the performance and operation of the control device 602. The IC 802 can include a system management bus (SMBus) and a fuel gauge IC configured to support the smart battery data (SBData) commands and charge-control functions operable to control the charge device 700. The IC 802 can be coupled to an electrically erasable programmable read-only memory (EEPROM) for storing configuration information received from the fuel gauge IC, and the IC 802 can include a plurality of individual contacts 620a to 620e for Battery +, Battery −, Clock, Data and Thermistor, respectively. The contacts 620a, 620b, 620c, 620d and 620e are configured to interface with the contacts 704a, 704b, 704c, 704d and 704e, respectively, of a bay 702 of the charge device 700.

In one example operation, the control device 602 and bay 702 of a charge device 700 cooperate to raise the battery voltage above a threshold level by applying a trickle charge to battery, through the electrical contacts 620a to 620e and 704a to 704e, before applying a full charge. The IC 802 limits the full charge current applied by the charge device 700 to an amount that is less than or equal to the a designated maximum charge rate which can be 0.7V to 1V. Furthermore, the IC 802 can be programmed to control and limit the voltage rise within the battery 618 to, for example, to a range within four and two-tenths plus or minus five one-hundredths voltage per cell 4.2±0.05 V/cell while holing the battery voltage constant at a desired control level as the charge current decays and each of the cell's internal electromotive force (EMF) continues to rise.

As previously discussed, the charge device 700 includes a plurality of bays 702 to gang charge multiple control devices 600. The gang charging operations will typically employ the SMBus can be contained on separate control ICs such as, for example, the commercially available MAX1645, MAX1667 and LTC1759 control ICs. The charge device 700 includes a plurality of batter charger ICs, where each battery charger IC 804 is associated with a bay 702 of the charge device 700. In one embodiment, the battery charger IC 804 substantially conforms to the previously described smart battery charger standard, and particularly that of a Level 2 Smart Battery Charger. The battery charger IC 804 can operate as a slave device to controller 602 within the control device 600 such that the battery charger IC 804 within the charge device 700 does not initiate communication on the SMBus. However, each battery charger IC 804 within the charge device 700 can be adapted to receive commands and respond to queries for status information and can adjust its provided output characteristics in direct response to the commands and messages received from the control device 602.

VI. Alternate Head Gear Assemblies

Figure 11:
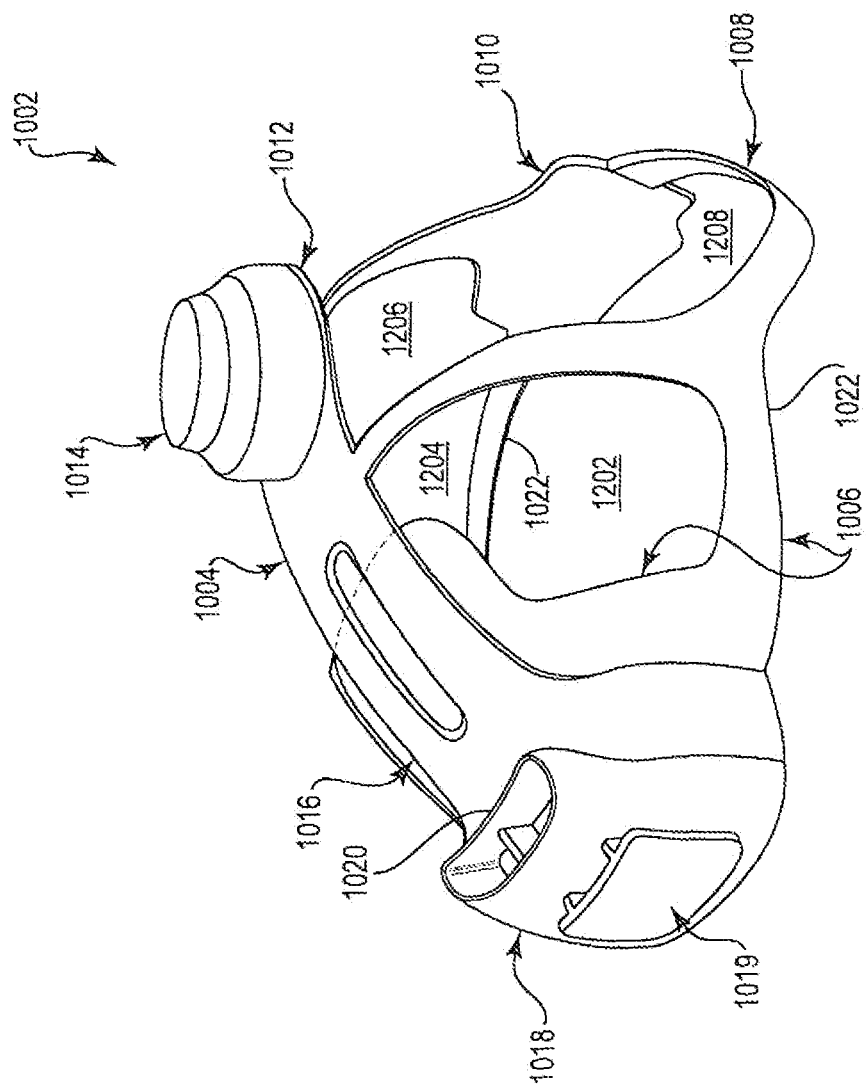
FIG. 11. is a side elevation perspective view of one alternate embodiment of the head hear assembly.

Referring to FIG. 11, in one embodiment, the head gear of the surgical protective assembly 100 includes a relatively light weight head gear assembly 1002. The head gear assembly 1002 includes a semi-rigid outer arm assembly 1004 which, in one embodiment, defines an air channel. The outer arm assembly 1004 is slidably and adjustably coupled to a semi-rigid inner arm assembly 1006. The inner arm assembly 1006 includes a flexible head band 1008 coupled to the outer arm assembly 1004, and the head band 1008 has a neck or lower head support member 1010. The outer arm assembly 1004, at end 1012, supports a fan, impeller or air movement device 1014. The end 1016 of the outer arm assembly 1004 has: (a) a flared shape with an increased diameter defining an air duct 1018; and (b) a lens mounting plate or face shield mount 1019. The air duct 1018 defines an inner air space fluidly connected to the air channel of the outer arm assembly 1004, and the air duct 1018 has a upper opening 1020 and a lower opening (now shown). The face shield mount 1019 has members configured to mate with a face shield (such as face shield 300) to enable the shield to be slidably connectable to the head gear assembly 1002 for proper attachment.

In operation, the user adjustably attaches the head gear assembly 1002 to the user's head by adjusting the side straps 1022 of the head band 1008 by turning a thumb wheel (not shown) coupled to the occipital support member 1010. This adjustment is made by either increasing or decreasing the length of the side straps 1022 and ultimately affecting the circumference of the head gear assembly 1002. Once secured and placed in operating mode, the air movement device 1014 moves air through the outer arm assembly 1004 to the air duct 1018, causing air to flow though the opening 1020 and the lower opening (not shown) of the air duct 1018. As a result, air flows over the face of the user, supplying the user with fresh air. The air also flows through opening 1020 to supply air to the top of the user's head for cooling.

In another embodiment, the outer arm assembly 1004 does not define a channel. Here, the surgical hood (such as hood 502) includes an elongated air duct. When the surgical hood is attached to the head gear assembly 1002, the elongated air duct of the hood brings the air movement device 1014 into fluid communication with the opening 1020 of the air duct 1018.

Figure 12:
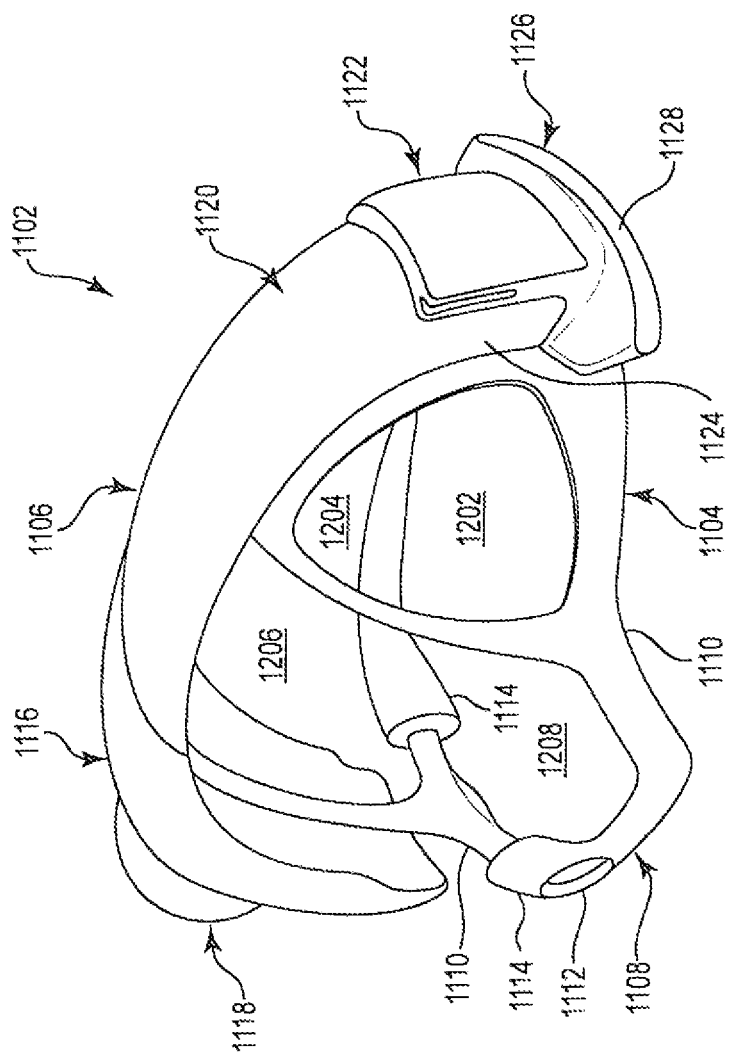
FIG. 12. is a side elevation perspective view of another alternate embodiment of the head hear assembly.

Referring to FIG. 12, in one embodiment, the head gear of the surgical protective assembly 100 includes a relatively light weight head gear assembly 1102. The head gear assembly 1102 includes a semi-rigid head securing device 1104 coupled to a hollow wall, duct member or plenum 1106 which defines an air channel. The head securing device 1104 includes a flexible head band 1108 which has plurality of side straps 1110. The rear side strap section 1112 supports a plurality of resilient comfort members 1114, such as foam members, configured to engage the user's neck or lower head region.

The plenum 1106, at end 1116, supports a fan, impeller or air movement device 1118. The end 1120 of the plenum 1106 has: (a) a flared shape with an increased diameter defining an air duct 1122; (b) a filter holder 1124; and (c) a lens mounting plate or face shield mount 1126. The air duct 1122 defines an inner air space fluidly connected to the air channel of the plenum 1106, and the air duct 1022 has a lower opening 1128. The face shield mount 1126 has members configured to mate with a face shield (such as face shield 300) to enable the shield to be removably connectable to the head gear assembly 1102 for proper attachment.

In operation, the user adjustably attaches the head gear assembly 1102 to the user's head by adjusting the side straps 1110 of the head band 1104 by turning a thumb wheel (not shown) coupled to the rear portion of the head band 1104. This adjustment is made by either increasing or decreasing the length of the side straps 1110 and ultimately affecting the circumference of the head gear assembly 1102. Once secured and placed in operating mode, the air movement device 1118 moves air through the plenum 1106 to the air duct 1122, causing air to flow though the opening 1128 of the air duct 1122. As a result, air flows over the face of the user, supplying the user with fresh air.

Each of the head gear assemblies 1002 and 1102 is relatively light weight and made of relatively few parts. For example, the framework of each assembly 1002 and 1102 defines relatively large spaces or open areas 1202, 1204, 1206 and 1208. These open areas 1202, 1204, 1206 and 1208 leave a substantial portion of the user's head uncovered by the assemblies 1002 and 1102, and this also results in a relatively light weight configuration decreasing the load on the user's head.

In one embodiment, each of the head gear assemblies 1002 and 1102 includes all or some of the parts, components and elements of the head gear assembly 200. It should be understood that any of the embodiments (or portions thereof) described herein can be interchanged or combined to form other suitable embodiments of the surgical protective head gear assembly.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method for manufacturing a surgical head gear assembly, the method comprising:
    (a) providing an inner wall having a lip suitable for coupling via removable snap-fit arrangement with a lip on an outer wall so that: (i) there is a passage between the outer wall and inner wall; and (ii) the coupled outer and inner walls have a first end, a second end, and an opening substantially adjacent to the first end wherein the opening is fluidly connected to the passage;
    (b) forming a different opening in the outer wall so that the different opening is fluidly connected to the passage;
    (c) forming a plurality of additional openings in the inner wall so that the additional openings are fluidly connected to the passage;
    (d) coupling the lip on outer wall to the lip on the inner wall via snap-fit arrangement.

2. The method of claim 1, further comprising coupling an air delivery device to the inner wall.

3. The method of claim 2 wherein the head gear assembly is defined by a visor portion, a crown portion distal the visor portion, lateral portions distal the visor portion and adjacent the crown portion, and a rear portion distal the crown portion wherein the air delivery device is oriented in the crown portion of the head gear assembly.

4. The method of claim 2 wherein the air delivery device comprises a plurality of blades.

5. The method of claim 4 wherein the blades are air foil shaped.

6. The method of claim 5 wherein the air foil shaped blades are further defined by a leading parabolic wall, a trailing wall, and a top wall; the trailing parabolic wall joining the leading parabolic wall at an inner vertical edge; the top wall having a partially triangular shaped region with a vertex wherein such vertex meets the trailing wall.

7. The method of claim 1, further comprising coupling a cord guide to the air delivery device.

8. The method of claim 1, further comprising causing the outer wall to have a face shield mount substantially adjacent to the first end.

9. The method of claim 1, further comprising coupling a head securing apparatus to the inner wall.

10. The method of claim 9, further comprising coupling a tensioner to the inner wall.

11. The method of claim 1, further comprising causing the additional openings to be distributed over an area of the inner wall in a designated pattern.

12. The method of claim 11, further comprising causing the additional openings to be distributed on the area of the inner wall in a uniform array.

* * * * *